US007078424B2

(12) United States Patent
Hamilton et al.

(10) Patent No.: US 7,078,424 B2
(45) Date of Patent: Jul. 18, 2006

(54) N-LINKED SULFONAMIDES OF N-HETEROCYCLIC CARBOXYLIC ACIDS OR CARBOXYLIC ACID ISOSTERES

(75) Inventors: Gregory S. Hamilton, Catonsville, MD (US); Mark H. Norman, Thousand Oaks, CA (US); Yong-Qian Wu, Columbia, MD (US)

(73) Assignee: GPI NIL Holdings, Inc., Baltimore, MD (US)

( * ) Notice: Subject to any disclaimer, the term of this patent is extended or adjusted under 35 U.S.C. 154(b) by 7 days.

(21) Appl. No.: 10/601,607

(22) Filed: Jun. 24, 2003

(65) Prior Publication Data

US 2004/0082622 A1   Apr. 29, 2004

Related U.S. Application Data

(60) Continuation of application No. 09/791,660, filed on Feb. 26, 2001, now abandoned, which is a division of application No. 09/204,236, filed on Dec. 3, 1998.

(60) Provisional application No. 60/087,842, filed on Jun. 3, 1998.

(51) Int. Cl.
A61K 31/41 (2006.01)
C07D 403/04 (2006.01)

(52) U.S. Cl. ...... 514/381; 514/359; 514/361; 514/362; 514/363; 514/364; 514/369; 514/379; 514/380; 514/382; 514/383; 514/384; 514/389; 548/128; 548/132; 548/183; 548/226; 548/243; 548/250; 548/251; 548/255; 548/259; 548/262.2; 548/263.2; 548/314.7; 548/542; 548/545; 548/565

(58) Field of Classification Search ........ 514/359, 514/361, 362, 363, 364, 369, 379, 380, 381, 514/382, 383, 384, 389; 548/128, 132, 183, 548/226, 243, 250, 251, 255, 259, 262.2, 548/263.2, 314.7, 542, 545, 565
See application file for complete search history.

(56) References Cited

U.S. PATENT DOCUMENTS

| 3,277,087 A | 10/1966 | Wei et al. |
| 3,424,749 A | 1/1969 | Pfenninger |
| 3,501,512 A | 3/1970 | Wei et al. |
| 3,890,311 A | 6/1975 | Wei et al. |
| 4,070,361 A | 1/1978 | Petrillo, Jr. |
| 4,217,130 A | 8/1980 | Tsuruta |
| 4,374,829 A | 2/1983 | Harris et al. |
| 4,377,521 A | 3/1983 | Holland |
| 4,390,695 A | 6/1983 | Krapcho et al. |
| 4,472,380 A | 9/1984 | Harris et al. |
| 4,578,474 A | 3/1986 | Krapcho et al. |
| 4,593,102 A | 6/1986 | Shanklin, Jr. |
| 4,596,819 A | 6/1986 | Nicolaides et al. |
| 4,642,348 A | 2/1987 | Shanklin, Jr. et al. |
| 4,692,458 A | 9/1987 | Ryan et al. |
| 4,734,420 A | 3/1988 | Ryan et al. |
| 4,745,124 A | 5/1988 | Ryan et al. |
| 4,943,570 A | 7/1990 | Constansa et al. |
| 5,002,963 A | 3/1991 | De Luca et al. |
| 5,002,964 A | 3/1991 | Loscalzo |
| 5,071,844 A | 12/1991 | Alker et al. |
| 5,128,483 A | 7/1992 | Trybulski et al. |
| 5,166,317 A | 11/1992 | Wallace et al. |
| 5,192,773 A | 3/1993 | Armistead et al. |
| 5,214,034 A | 5/1993 | Nakayama et al. |
| 5,215,969 A | 6/1993 | Springer et al. |
| 5,232,923 A | 8/1993 | Fukazawa et al. |
| 5,330,993 A | 7/1994 | Armistead et al. |
| 5,342,942 A | 8/1994 | Jaen et al. |
| 5,359,138 A | 10/1994 | Takeuchi et al. |
| 5,403,850 A | 4/1995 | Imaki et al. |
| 5,453,437 A | 9/1995 | Schohe et al. |
| 5,463,007 A | 10/1995 | Pinschmidt et al. |
| 5,472,687 A | 12/1995 | Proctor |
| 5,504,197 A | 4/1996 | Schubert et al. |
| 5,506,243 A | 4/1996 | Ando et al. |
| 5,516,797 A | 5/1996 | Armistead et al. |
| 5,519,134 A | 5/1996 | Acevedo et al. |
| 5,536,737 A | 7/1996 | Kobayashi et al. |
| 5,543,423 A | 8/1996 | Zelle et al. |
| 5,571,832 A | 11/1996 | De Costa et al. |
| 5,585,397 A | 12/1996 | Tung et al. |
| 5,599,927 A | 2/1997 | Or et al. |
| 5,604,294 A | 2/1997 | Luly et al. |
| 5,614,547 A | 3/1997 | Hamilton et al. |
| 5,620,971 A | 4/1997 | Armistead et al. |
| 5,627,285 A | 5/1997 | Hanko |
| 5,629,325 A | 5/1997 | Lin et al. |
| 5,646,167 A | 7/1997 | MacPherson et al. |
| 5,663,174 A | 9/1997 | Dumont et al. |

(Continued)

FOREIGN PATENT DOCUMENTS

DE   2505114   8/1976

(Continued)

OTHER PUBLICATIONS

Van Den Broek, "Assymmetric diels-alder . . . " CA 100:191690 91984).

(Continued)

Primary Examiner—Celia Chang
(74) Attorney, Agent, or Firm—Foley & Lardner

(57) ABSTRACT

This invention relates to novel N-linked sulfonamides of N-heterocyclic carboxylic acid and carboxylic acid isosteres, their preparation, and use for treating neurological disorders including physically damaged nerves and neurodegenerative diseases, and for treating alopecia and promoting hair growth.

7 Claims, 3 Drawing Sheets

U.S. PATENT DOCUMENTS

| | | | |
|---|---|---|---|
| 5,665,774 A | 9/1997 | Armistead et al. |
| 5,696,135 A | 12/1997 | Steiner et al. |
| 5,703,088 A | 12/1997 | Sharpe et al. |
| 5,714,510 A | 2/1998 | Proctor |
| 5,717,092 A | 2/1998 | Armistead et al. |
| 5,721,256 A | 2/1998 | Hamilton et al. |
| 5,744,485 A | 4/1998 | Zelle et al. |
| 5,780,484 A | 7/1998 | Zelle et al. |
| 5,786,378 A | 7/1998 | Hamilton et al. |
| 5,795,890 A | 8/1998 | Nakae |
| 5,795,908 A | 8/1998 | Hamilton et al. |
| 5,798,355 A | 8/1998 | Steiner et al. |
| 5,801,187 A | 9/1998 | Li et al. |
| 5,801,197 A | 9/1998 | Steiner et al. |
| 5,811,434 A | 9/1998 | Zelle |
| 5,840,736 A | 11/1998 | Zelle |
| 5,843,960 A | 12/1998 | Steiner et al. |
| 5,846,979 A | 12/1998 | Hamilton et al. |
| 5,846,981 A | 12/1998 | Steiner et al. |
| 5,859,031 A | 1/1999 | Hamilton et al. |
| 5,869,725 A | 2/1999 | Gennari |
| 5,874,449 A | 2/1999 | Hamilton et al. |
| 5,898,029 A | 4/1999 | Lyons et al. |
| 6,121,258 A | 9/2000 | Pikul et al. |
| 6,121,272 A | 9/2000 | Almstead et al. |
| 6,268,384 B1 | 7/2001 | Novak |

FOREIGN PATENT DOCUMENTS

| | | |
|---|---|---|
| DE | 3636278 | 10/1986 |
| DE | 4425950 | 1/1996 |
| DE | 197 42 263 | 9/1997 |
| EP | 088350 | 9/1983 |
| EP | 419049 | 3/1991 |
| EP | 443983 | 8/1991 |
| EP | 471135 | 2/1992 |
| EP | 476933 | 3/1992 |
| EP | 488 258 | 6/1992 |
| EP | 494005 | 7/1992 |
| EP | 519819 | 12/1992 |
| EP | 557842 | 2/1993 |
| EP | 0 610 744 A | 8/1994 |
| EP | 769498 | 4/1997 |
| EP | 823419 | 2/1998 |
| JP | 55-153763 | 11/1980 |
| JP | 64-19063 | 1/1989 |
| JP | 03-181475 | 8/1991 |
| JP | 05-194235 | 8/1993 |
| JP | 09-169758 | 6/1997 |
| WO | WO 85/04577 | 10/1985 |
| WO | WO 88/00040 | 1/1988 |
| WO | WO 88/09789 | 12/1988 |
| WO | WO 89/06234 | 7/1989 |
| WO | WO 92/00278 | 1/1992 |
| WO | WO 92/04370 | 3/1992 |
| WO | WO 92/11245 | 7/1992 |
| WO | WO 92/11850 | 7/1992 |
| WO | WO 92/19745 | 11/1992 |
| WO | WO 92/21313 | 12/1992 |
| WO | WO 92 21313 A | 12/1992 |
| WO | WO 93/05014 | 3/1993 |
| WO | WO 93/14762 | 5/1993 |
| WO | WO 93/14072 | 7/1993 |
| WO | WO 93/18736 | 9/1993 |
| WO | WO 92/19593 | 11/1993 |
| WO | WO 93/25546 | 12/1993 |
| WO | WO 94/03476 | 2/1994 |
| WO | WO 94/05639 | 3/1994 |
| WO | WO 94/12474 | 6/1994 |
| WO | WO 94/13629 | 6/1994 |
| WO | WO 94/14428 | 7/1994 |
| WO | WO 94/15900 | 7/1994 |
| WO | WO 95/12398 | 5/1995 |
| WO | WO 95/12572 | 5/1995 |
| WO | WO 95/24385 | 9/1995 |
| WO | WO 95/34303 | 12/1995 |
| WO | WO 95/35308 | 12/1995 |
| WO | WO 95/35367 | 12/1995 |
| WO | WO 96/06846 | 3/1996 |
| WO | WO 96/11195 | 4/1996 |
| WO | WO 96/20725 | 7/1996 |
| WO | WO 96/20949 | 7/1996 |
| WO | WO 96/33175 | 10/1996 |
| WO | WO 96/33184 | 10/1996 |
| WO | WO 96 40140 A | 12/1996 |
| WO | WO 96/40633 | 12/1996 |
| WO | WO 96/41609 | 12/1996 |
| WO | WO 97/23202 | 3/1997 |
| WO | WO 97/23458 | 3/1997 |
| WO | WO 97/36869 | 9/1997 |
| WO | WO 97/38008 | 10/1997 |
| WO | WO 97/48681 | 12/1997 |
| WO | WO 97/49695 | 12/1997 |
| WO | WO 98/13343 | 2/1998 |
| WO | WO 98/08814 | 3/1998 |
| WO | WO 98 08827 A | 3/1998 |
| WO | WO 98/37885 | 3/1998 |
| WO | WO 98/08827 | 5/1998 |
| WO | WO 98/20891 | 5/1998 |
| WO | WO 98/20892 | 5/1998 |
| WO | WO 98/20893 | 5/1998 |
| WO | WO 98/22432 | 5/1998 |
| WO | WO 98/29117 | 9/1998 |
| WO | WO 99/45006 | 9/1998 |
| WO | WO 98/55091 | 10/1998 |
| WO | WO 98/24805 | 11/1998 |
| WO | WO 98 55090 A | 12/1998 |
| WO | WO 99/10340 | 3/1999 |
| WO | WO 99/14998 * | 4/1999 |
| WO | WO 99/45006 | 9/1999 |
| WO | WO 00/58280 | 3/2000 |
| WO | WO 00/58285 | 3/2000 |
| WO | WO 00/58304 | 3/2000 |

OTHER PUBLICATIONS

Nkunya et al., "Assymmetric synthesis of alpha . . . " CA 106:67013 (1985).

Thorsett et al., "Preparation of N-sulfonylproline dipeptide . . . " CA 130:168662 (1999).

Durette et al., "Preparation of heterocylci dipeptide . . . " CA 130:52724 (1998).

King, "Bioisoteres, conformation restriction . . . " Med. Chem. Principle and Practice, (1994) p. 206-209.

Patani et al., "Bioisoterism: a rational approach in drug design" Chem. Rev. v.96, 3147-76 (1996).

Ponticello et al., "Synthesis of 2- and 6-chloro . . . " CA 93:186222 (1980).

Saunders et al., "Novel quinuclidine-based . . . " CA 112:158157 (1990).

Magal, "Method for treating hearing loss . . . " CA 130:262139 (1999).

Supplementary Partial European Search Report, Mar. 19, 2002.

Moss, et al.: "2-Amino Ketene S,S-Acetals as α-Amino Acid Homoenolate Equivalents. Synthesis of 3-Substituted Prolines and Molecular Structure of 2-(N-Pivaloylprrolidin-2-ylidene)-1.3-dithiane"; J. CHEM. SOC. PERKIN TRANS. 1(1992), (20), pp. 2615-2624.

King, Frank D., "Bioisosteres, Conformational Restriction, and Pro-Drugs—Case History: An Example of a Conformational Restriction Approach," *Med. Chem.: Prin. & Prac.*, 1994, 206-09.

Gudasheva, T.A. et al., "Synthesis and antiamnesic activity of a series of N-acylprolyl-containing dipeptides," *Eur. J. Med. Chem.*, 31 (1996), 151-7.

Dawson, T. et al., "Immunosuppressant RK506 enhances phosphorylation of nitric oxide synthase and protects against glutamate neurotoxicity," *Proc. Nat. Acad. Sci.*, 1993, 90, 9808-12.

Dawson, T. et al., "The immunophillins, FK506 binding protein and cyclophilin, are discretely localized in the brain: relationship to calcineurin," *Neuroscience*, 1994, 62, 569-80.

Gold, B. et al., "Regulation of the Transcription Factor c-JUN by nerve growth factor in adult sensory neurons," *Neuroscience Letters*, 1993, 154, 129-33.

Gold, B. et al., "Regulation of aberrant neurofilament phosphorylation in neuronal perikarya. IV. Evidence for the involvement of two signals," *Brain Research*, 1993, 626, 23-30.

Gold, B. et al., "The Immunosuppressant FK506 increases functional recovery and nerve regeneration following peripheral nerve injury," *Restorative Neurology and Neuroscience*, 1994, 6, 287-96.

Gold, B. et al., "Multiple signals underlie the axotomy-induced up-regulation of c-JUN in adult sensory neurons," *Neuroscience Letters*, 1994, 176, 123-27.

Gold, B. et al., "The immunosuppressant FK506 increases the rate of axonal regeneration in rat sciatic nerve," *J. Neuroscience*, 15 (1995) 7509-16.

Hamilton, Gary S. and Steiner, Joseph P., "Neuroimmunophilin Ligands as Novel Therapeutics for the Treatment of Degenerative Disorders of the Nervous System," 1-71.

Holt, Dennis A. et al., "Structure-activity of synthetic FKBP ligands as peptidyl-prolyl isomerase inhibitors," *Bioorg. Med. Chem. Lett.*, 1994, 4(2), 315-20.

Iwabuchi, Tokuro et al., "Effects of immunosuppressive peptidyl-prolyl cis-trans isomerase (PPiase) inhibitors, cyclosporin A, FK506, ascomycin and rapamycin, on hair growth initiation in mouse: immunosuppression is not required for new hair growth," *J. Dermatol. Sci.*, 1995, 9, 64-69.

Jiang, Hong et al., "Induction of Anagen in Telogen Mouse Skin by Topical Application of FK506, a Potent Immunosuppressant," *J. Invest. Dermatol.*, 1995, 104, 523-25.

Kitamura et al., "Suppressive Effect of FK-506, a Novel Immunosuppressant, Against MPTP-Induced Dopamine Depletion in the Striatum of Young C57BL/6 Mice," *J. Neuroimmunology*, 1994, 50, 221-24.

Lyons, W.E. et al., "Immunosuppressant FK506 promotes neurite outgrowth in cultures of PC 12 cells and sensory ganglia," *Proc. Nat. Acad. Sci.*, 1994, 91, 3191-95.

Lyons, W.E. et al., "Neuronal Regeneration Enhances the Expression of the Immunophilin FKBP-12," *J. Neuroscience*, 1995, 15(4), 2985-94

Ryba et al., "Cyclosporine A Prevents Neurological Deterioration of Patients with SAH—A Preliminary Report," *Acta Neurochirurgica*, 1991, 112, 25-27.

Shiga et al., "Cyclosporin A Protects Against Ischemia-Reperfusion Injury in the Brain," *Brain Research*, 1992, 595, 145-48.

Snyder, S. and Sabatini, D., "Iminunophilins and the Nervous System," *Nature Medicine*, 1995, 1, 32-37.

Steiner, J. et al., "High brain densities of the Immunophilin FKBP colocalized with calcineurin," *Nature*, 358 (1992) 584-7.

Steiner, J. et al., "Nonimmunosupressive ligands for neuroirnmunophilins promote nerve extension in vitro and in vivo," *Society for Neuroscience Abstracts*, 1996, 22, 297.

Steiner, J. et al., "Neurotrophic immunophilin ligands stimulate structural and functional recovery in neurodegenerative animal models," *Proc. Nat. Acad. Sci.*, 1997, 94, 2019-24.

Steiner, J. et al., "Neurotrophic actions of nonimmunosuppressive analogues of immunosuppressive drugs FK506, rapamycin and cyclosporin A," *Nature Medicine*, 1997, 421-28.

Teichner et al., "Treatment with Cyclosporin A Promotes Axonal Regeneration in Rats Submitted to Transverse Section of the Spinal Cord," *Int'l J. Brain Research & Neurobio.*, 1993, 34(3), 343-349.

Yamamoto, Satoshi et al., "Stimulation of Hair Growth by Topical Application of FK506, a Potent Immunosuppressive Agent," *J. Invest. Dermat.*, 1994, 102(2), 160-64.

Hagitani, Chemical Abstracts, vol. 128:34575, 1997.
MacPherson, Chemical Abstracts, vol. 97:88995, 1997.
Katz, Chemical Abstracts, vol. 127:346178, 1997.
Fernandez-Megia, Chemical Abstracts, vol. 127:66115, 1997.
Chen, Chemical Abstracts, vol. 127:354894, 1997.
MacPherson, Chemical Abstracts, vol. 125:347383, 1996.
MacPherson, Chemical Abstracts, vol. 125:34156, 1996.
Brueckner, Chemical Abstracts, vol. 125:52625, 1996.
Soe, Chemical Abstracts, vol. 124:260885, 1996.
Takeuchi, Chemical Abstracts, vol. 125:222388, 1996.
Boehn, Chemical Abstracts, vol. 124:233168, 1996.
MacPherson, Chemical Abstracts, vol. 95:88473.
Ishida, Chemical Abstracts, vol. 124:20624, 1995.
Reilly, Chemical Abstracts, vol. 123:8863, 1995.
Takeuchi, Chemical Abstracts, vol. 124:20631, 1995.
Takeuchi, Chemical Abstracts, vol. 122:234609, 1995.
MacPherson, Chemical Abstracts, vol. 122:314456, 1995.
Fernandez—Megia, Chemical Abstracts, vol. 122:31909, 1995.
Kimura, Chemical Abstracts, vol. 123:9413, 1995.
Matsubara, Chemical Abstracts, vol. 121:275875, 1994.
Teramoto, Chemical Abstracts, vol. 119:140193, 1993.
Okabe, Chemical Abstracts, vol. 120:260511, 1994.
Manickurn, Chemical Abstracts, vol. 122:159795, 1995.
Yamanaka, Chemical Abstracts, vol. 93:109096, 1993.
Fujii, Chemical Abstracts, vol. 93:10520, 1993.
Yamanaka, Chemical Abstracts, vol. 93:1516, 1993.
Yu, Chemical Abstracts, vol. 119:285511, 1993.
Na, Chemical Abstracts, vol. 122:81924, 1995.
Cserhati, Chemical Abstracts, vol. 119:151373, 1993.
Toyooka, Chemical Abstracts, vol. 120:26665, 1994.
Gamo, Chemical Abstracts, vol. 117:211689, 1992.
Ishikawa, Chemical Abstracts, vol. 117:251242, 1992.
Hayakawa, Chemical Abstracts, vol. 92:70434, 1992.
Moss, Chemical Abstracts, vol. 118:7348, 1993.
O'Connell, Chemical Abstracts, vol. 117:111216, 1992.
Sardina, Chemical Abstracts, vol. 117:234474, 1992.
Ibrahim, Chemical Abstracts, vol. 116:174748, 1992.
Yamanaka, Chemical Abstracts, vol. 116:83541, 1992.
Ito, Chemical Abstracts, vol. 115:49085, 1991.
Hawayaka, Chemical Abstracts, vol. 91:5253, 1991.
Cserhati, Chemical Abstracts, vol. 115:173812, 1991.

Varga, Chemical Abstracts, vol. 117:277, 1992.
Gamoh, Chemical Abstracts, vol. 114:220443, 1991.
Fujii, Chemical Abstracts, vol. 114:102053, 1991.
Yoshioka, Chemical Abstracts, vol. 114:74531, 1991.
Tomari, Chemical Abstracts, vol. 90:61403, 1990.
Hayakawa, Chemical Abstracts, vol. 90:6088, 1990.
Collins, Chemical Abstracts, vol. 113:96679, 1990.
Zhou, Chemical Abstracts, vol. 113:152181, 1990.
Simmaco, Chemical Abstracts, vol. 113:55213, 1990.
Mostovnikov, Chemical Abstracts, vol. 114:55033, 1991.
Ejima, Chemical Abstracts, vol. 113:78788, 1990.
Fujiwawa, Chemical Abstracts, vol. 112:35875, 1990.
Tomari, Chemical Abstracts, vol. 112:179020, 1990.
Iwakuma, Chemical Abstracts, vol. 89:66056, 1989.
Lubell, Chemical Abstracts, vol. 111:115731, 1989.
Langlois, Chemical Abstracts, vol. 112:178424, 1990.
Nishi, Chemical Abstracts, vol. 112:131596, 1990.
Otto, Chemical Abstracts, vol. 115:136711, 1991.
Belenkii, Chemical Abstracts, vol. 111:146061, 1989.
Ryan, Chemical Abstracts, vol. 110:147868, 1989.
Hayakawa, Chemical Abstracts, vol. 110:8191, 1989.
Takemura, Chemical Abstracts, vol. 11:75160, 1989.
Hayakawa, Chemical Abstracts, vol. 109:211064, 1988.
Tagawa, Chemical Abstracts, vol. 88:67487, 1988.
Bellattar, Chemical Abstracts, vol. 88:21212, 1988.
Bhushan, Chemical Abstracts, vol. 110:131593, 1989.
Shono, Chemical Abstracts, vol. 109:118111, 1988.
McClung, Chemical Abstracts, vol. 109:69689, 1988.
Tagawa, Chemical Abstracts, vol. 107:176302, 1987.
Atarashi, Chemical Abstracts, vol. 108:131711, 1988.
Reitsma, Chemical Abstracts, vol. 106:112841, 1987.
Slegel, Chemical Abstracts, vol. 108:197550, 1988.
Kasai, Chemical Abstracts, vol. 107:129386, 1987.
Imal, Chemical Abstracts, vol. 107:168033, 1987.
Takeuchi, Chemical Abstracts, vol. 108:205042, 1988.
Hayakawa, Chemical Abstracts, vol. 106:119895, 1987.
Belattar, Chemical Abstracts, vol. 106:219573, 1987.
Takeda, Chemical Abstracts, vol. 105:153560, 1986.
Iwakuma, Chemical Abstracts, vol. 86:186669, 1986.
Wada, Chemical Abstracts. vol. 86:3609, 1986.
Moyer, Chemical Abstracts, vol. 106:18305, 1987.
Zaher, Chemical Abstracts, vol. 107:7583, 1987.
Levina, Chemical Abstracts, vol. 106:134510, 1987.
Voigt, Chemical Abstracts, vol. 107:97096, 1987.
Voigt, Chemical Abstracts, vol. 106:176825, 1987.
Bianchi-Bosisio, Chemical Abstracts, vol. 104:164657, 1986.
Shimizu, Chemical Abstracts, vol. 105:71819, 1986.
Takeda, Chemical Abstracts, vol. 104:109698, 1986.
Iwakuma, Chemical Abstracts, vol. 104:88453, 1986.
Cupps, Chemical Abstracts, vol. 103:178594, 1985.
Maeda, Chemical Abstracts, vol. 103:123873, 1985.
Muramoto, Chemical Abstracts, vol. 103:88190, 1985.
Liao, Chemical Abstracts, vol. 103:101248, 1985.
Barluenga, Chemical Abstracts, vol. 104:50514, 1986.
Wada, Chemical Abstracts, vol. 101:151603, 1984.
Maurer, Chemical Abstracts, vol. 100:86080, 1984.
Clark, Chemical Abstracts, vol. 100:156954, 1984.
Miyaguchi, Chemical Abstracts, vol. 101:226284, 1984.
Fujisawa, Chemical Abstracts, vol. 100:120622, 1984.
Yoshihara, Chemical Abstracts, vol. 99:23012, 1983.
Sakurai, Chemical Abstracts, vol. 98:10774, 1983.
Condon, Chemical Abstracts, vol. 96:97142, 1982.
Koroleva, Chemical Abstracts, vol. 97:145238, 1982.
Ryan, Chemical Abstracts, vol. 96:143321, 1982.
Voelter, Chemical Abstracts, vol. 97:24249, 1982.
Evans, Chemical Abstracts, vol.95:24122, 1981.
El-Naggar, Chemical Abstracts, vol. 96:163157, 1982.
Kyowa, Chemical Abstracts, vol. 94:208700, 1981.
Kyowa, Chemical Abstracts, vol. 96:56735, 1981.
Uchiyama, Chemical Abstracts, vol. 93:145695, 1980.
Tsuruta, Chemical Abstracts, vol. 92:141802, 1980.
Petrillo, Chemical Abstracts, vol 90:138199, 1979.
Busson, Chemical Abstracts, vol. 89:215152, 1978.
El-Nagger, Chemical Abstracts, vol. 90:122044, 1979.
El-Naggar, Chemical Abstracts, vol. 89:110311, 1978.
Bongiovanni, Chemical Abstracts, vol. 90:35753, 1979.
Karger, Chemical Abstracts, vol. 90:147896, 1979.
Metrione, Chemical Abstracts, vol. 89:180326, 1978.
Klimek, Chemical Abstracts, vol. 93:72234, 1980.
El-Naggar, Chemical Abstracts, vol. 88:121704, 1978.
Kusch, Chemical Abstracts, vol. 89:2490, 1978.
Mairanovskii, Chemical Abstracts, vol. 86:140428, 1977.
Hayes, Chemical Abstracts, vol. 85:137108, 1976.
Sudlow, Chemical Abstracts, vol. 86:37492, 1977.
Klimek, Chemical Abstracts, vol. 89:103031, 1978.
Klimek, Chemical Abstracts, vol. 89:102994, 1978.
Henry, Chemical Abstracts, vol. 84:31125, 1976.
Miyoshi, Chemical Abstracts, vol. 83:193088, 1975.
Fujii, Chemical Abstracts, vol. 83:43713, 1975.
Sudlow, Chemical Abstracts, vol. 84:69223, 1976.
Wyszynski, Chemical Abstracts, vol. 84:173364, 1976.
El-Naggar, Chemical Abstracts, vol. 83:43714, 1975.
Teichgraeber, Chemical Abstracts, vol. 81:11494, 1974.
Lapuk, Chemical Abstracts, vol. 81:4232, 1974.
Vigny, Chemical Abstracts, vol. 81:74341, 1974.
Rudinger, Chemical Abstracts, vol. 80:48358, 1974.
Klimek, Chemical Abstracts, vol. 81:91909, 1974.
Chimiak, Chemical Abstracts, vol. 79:115871, 1973.
Munier, Chemical Abstracts, vol. 78:58763, 1973.
Seiler, Chemical Abstracts, vol. 76:22671, 1972.
Wei, Chemical Abstracts, vol. 73:3947, 1970.
Muehle, Chemical Abstracts, vol. 69:52175, 1968.
Pfenninger, Chemical Abstracts, vol. 68:95874, 1968.
Schoellmann, Chemical Abstracts, vol. 68:69316, 1968.
Chen, Chemical Abstracts, vol. 67:40166, 1967.
Morse, Chemical Abstracts, vol. 64:13073d, 1966.
Geigy, Chemical Abstracts, vol. 64:11232h, 1966.
Vlad, Chemical Abstracts, vol. 64:8910b, 1966.
Geigy, Chemical Abstracts, vol. 64:8220d, 1966.
Geigy, Chemical Abstracts, vol. 64:6672h, 1966.
Geigy, Chemical Abstracts, vol. 64:6672d, 1966.
Seiler, Chemical Abstracts, vol. 62:7e, 1965.
Dwyer, Chemical Abstracts, vol. 59:7640c, 1964.
Ponomareva, Chemical Abstracts, vol. 59:6511b, 1964.
Kuhn, Chemical Abstracts, vol. 51:8006i, 1957.
Beilstein Registration No. 89347.
Beilstein Registration No. 89346.
Beilstein Registration No. 89345.
Beilstein Registration No. 36650.
Beilstein Registration No. 30852.
Beilstein Registration No. 30355.
Beilstein Registration No. 27462.
Brenner, Chemical Abstracts, vol. 126:225550, 1997.
Hanko, Chemical Abstracts, vol. 95:110464, 1995.
MacPherson, Chemical Abstracts, vol. 95:88473, 1995.
MacPherson, Chemical Abstracts, vol. 122:314456, 1994.
Hanko, Chemical Abstracts, vol. 120:217671, 1993.
Trost, Chemical Abstracts, vol. 119:202752, 1993.
Aahman, Chemical Abstracts, vol. 118:80750, 1992.

Pinschmidt, Chemical Abstracts, vol. 89:74314, 1987.
Pinschmidt, Chemical Abstracts, vol. 88:77582, 1987.
Pinschmidt, Chemical Abstracts, vol. 107:116414, 1986.
Pinschmidt, Chemical Abstracts, vol. 107:40526, 1986.
Pinschmidt, Chemical Abstracts, vol. 87:62109, 1987.
Pinschmidt, Chemical Abstracts, vol. 87:32322, 1987.
Air Products and Chemicals, Chemical Abstracts, vol. 106:177060, 1986.
Shono, Chemical Abstracts, vol. 99:87977, 1983.
Kyowa Hakko Kogyo Co., Ltd., Chemical Abstracts, vol. 94:208700, 1980.
Kyowa hakko Kogyo Co. Ltd., Chemical Abstracts, vol. 94:156735, 1980.
Adesogan, Chemical Abstracts, vol. 92:110942, 1979.
Kuwano, Chemical Abstracts, vol. 76:100005, 1971.
Kuwano, Chemical Abstracts, vol. 76:113179, 1971.
Wei, Chemical Abstracts, vol. 73:3791, 1970.
Wei, Chemical Abstracts, vol. 73:3790, 1970.
Wei, Chemical Abstracts, vol. 73:3793, 1970.
Wei, Chemical Abstracts, vol. 73:3792, 1970.
Wei, Chemical Abstracts, vol. 71:81154, 1969.
Wei, Chemical Abstracts, vol. 66:28803, 1966.
Chemical Abstracts, vol. 64:12677e.
Pravda, Beilstein Registration No. 44706 (1955).
Decrescenzo, Chemical Abstracts, vol. 128:167263.
Koo, Chemical Abstracts, vol. 128:61425.
Zollinger, Chemical Abstracts, vol. 126:334169.
Kojima, Chemical Abstracts, vol. 128:101960.
Kojima, Chemical Abstracts, vol. 128:88717.
Kojima, Chemical Abstracts, vol. 128:3701.
Nagahara, Chemical Abstracts, vol. 97:31713.
Harayama, Chemical Abstracts, vol. 126:277419.
Craig, Chemical Abstracts, vol. 128:167337.
Hiroi, Chemical Abstracts, vol. 127:80935.
Cooper, Chemical Abstracts, vol. 127:17744.
Littler, Chemical Abstracts, vol. -126:157674.
Takatani, Chemical Abstracts, vol. 125:33679.
Nagahara, Chemical Abstracts, vol. 96:106515.
Nakagawa, Chemical Abstracts, vol. 126:30930.
Tingoli, Chemical Abstracts, vol. 125:247671.
Kokima, Chemical Abstracts, vol. 125:316228.
Kojima, Chemical Abstracts, vol. 125:316349.
Miyawaki, Chemical Abstracts, vol. 125:316226.
Ibuka, Chemical Abstracts, vol. 123:169445.
Fujii, Chemical Abstracts, vol. 123:314472.
Sambyal, Chemical Abstracts, vol. 123:98549.
Ikeuchi, Chemical Abstracts, vol. 123:285785.
Larock, Chemical Abstracts, vol. 121:157491.
Renson, Chemical Abstracts, vol. 120:294521.
Roos, Chemical Abstracts, vol. 121:167365.
Manickum, Chemical Abstracts, vol. 122:159795.
Nagahara, Chemical Abstracts, vol. 120:107001.
Knight, Chemical Abstracts, vol. 120:54423.
Cooper, Chemical Abstracts, vol. 117:171212.
Aahman, Chemical Abstracts, vol. 118:80750.
Cooper, Chemical Abstracts, vol. 118:22104.
Toshimitsu, Chemical Abstracts, vol. 118:7085.
Trybulski, Chemical Abstracts, vol. 115:8572.
Trybulski, Chemical: Abstracts, vol. 91:22654.
Merlin, Chemical Abstracts, vol. 115:92678.
Manickum, Chemical Abstracts, vol. 117:47892.
Cooper, Chemical Abstracts, vol. 116:83582.
Takahashi, Chemical Abstracts, vol. 115:8231.
Rosini, Chemical Abstracts, vol. 115:29647.
Alker, Chemical Abstracts, vol. 115:29390.
Constansa, Chemical Abstracts, vol. 90:46562.
Trybulski, Chemical Abstracts, vol. 114:6196.
Langlois, Chemical Abstracts, vol. 112:178424.
McIntosh, Chemical Abstracts, vol. 109:148669.
Merlin, Chemical Abstracts, vol. 109:170689.
Frigola, Chemical Abstracts, vol. 109:37817.
Hendrie, Chemical Abstracts, vol. 109:6914.
Shanklin, Chemical Abstracts, vol. 86:32892.
Elslager, Chemical Abstracts, vol. 101:230467.
Kaszubska, Chemical Abstracts, vol. 101:54832.
Yamashita, Chemical Abstracts, vol. 97:24187.
Holland, Chemical Abstracts, vol. 79:6866.
Holland, Chemical Abstracts, vol. 78:62679.
Koehler, Chemical Abstracts, vol. 87:134938.
Tseng, Chemical Abstracts, vol. 87:68603.
Holland, Chemical Abstracts, vol. 86:89409.
Holland, Chemical Abstracts, vol. 74:49083.
Wiegrebe, Chemical Abstracts, vol. 83:9671.
Holland, Chemical Abstracts, vol. 77:48046.
Hite, Chemical Abstracts, vol. 75:140649.
Shafi'ee, Chemical Abstracts, vol. 70:96027.
Shafi'ee, Chemical Abstracts, vol. 68:77541.
CA61:16145e.
CA60:8034h.
304403 *Beilstein*.
292-57 *Beilstein*.
Ahman, Jens and Somfai, "Preparation and Intramolecular Radical Cyclization of Some Cyclic N-Sulfonylenamines," *J. Chem. Soc., Perkin Trans. 1*. 1994, 8, 1079-82.
Aketa, Kohichi et al., "Stereochemical Studies. XL. A Biomimetic Conversion of L-Lysine into Optically Active 2-Substituted Piperidines. Synthesis of D- and L-Pipecolic acid, and (S)-(+)-Conline From L-Lysine." *Chem Pharm. Bull.*, 24(4), 1976, 621-31.
Alfes, H. et al., "Use of Mass Spectrometry for Identifying Central Nervous System-Stimulating Drugs (Doping Agents) Through Their DANS Derivatives." *Sportarzt Sportmed.*, 22(5), 1971, 104-5. (In German).
Alo, Babjide I. et al., "N-(Arylsulfonyl) tetrahydropyridinium Salts: Intermediates for Multi-Ring Heterocycles. Part I. Synthesis of Hexahydropyrido[1.2-b][1,2,4]benzo-thiadiazine Dioxides," *J. Chem. Soc. Perkin Trans. 1*, 1990, 7, 1835-38.
Alo, Babjida I. et al., "Synthesis of 1,2,4-Benzothiadiazines Via Readily Generated Iminium ions," *J. Chem. Soc., Perkin Trans. 1*, 1986, 5, 805-08.
Artico, Marino et al., "Synthesis of Pyrryl Aryl Sulfones Targeted at the HIV-1 Reverse Transcriptase," *Arch. Pharm.*, 1995, 328(3), 223-9.
Baumgarten et al., Hoppe-Seyler's Z. Physiol. Chem., 1932, 209(145), 159. (Beilstein Registration Nos. 12360).
H. Bayard Milne and Chi-Hsieh Pang. "Use of Benzylsulfonyl Chloride in Peptide Synthesis," *Chem. Abstr.*, 1957, 51: 10375i.
Brown, Dearg S. et al., "Substitution Reactions of 2-(Phenylsulfonyl) Piperidines and -Pyrrolidines With Carbon Nucleophiles: Synthesis of the Pyrrolidine Alkaloids Norruspoline and Ruspoline," Tetrahedron, (1991), 47(7), 1311-28.
Busson, R. and Vanderhaeghe, H., "Synthesis and Circular Dichroism of (5S)-1-Azabicyclo{3,2,0}Heptan-7-one." *J. Org. Chem.*, 43(23), 1978, 4438-41.

Collins, Mark A. and Jones, D. Neville, "Efficient Synthesis of Bicyclo [2,2,1] Heptane Derivatives Via Stereoselective Intramolecular Michael Reactions of Vinyl Sulfones." *Tetrahedron*, 52(26), 1996, 8795-8806.

Davis, Franklin A. et al., "Chiral Sulfamidas: Synthesis of Optically Active 2-Sulfamyloxazindines. High Enantioselectivity in the Asymmetric oxidation of sulfides to Sulfoxides." *J. Org. Chem.*, 49(8), 1984, 1465-67.

DeRuiter, Jack et al., "In Vitro Aldose Reductase Inhibitory Activity of Substituted N-Benzenesulfonyl-glycine Derivatives," *J. Pharm. Sci.*, 1987, 76(2), 149-52.

Dokuzovic, Zdravko et al., "Asymmetric Synthesis. Metal Complex Mediated Synthesis of Chiral Glycine by Enantioselective Proton Exchange." *J. Am. Chem. Soc.*, 108(8), 1986, 2034-39.

Ejima, Akio et al., "Antitumor Agents. 1. Asymmetric Synthesis of (S)-Camptothecin," *Tetrahedron Lett.*, 1989, 30(20), 2639-40.

El-Naggar, A.M. et al., "Synthesis and Biological Activity of Some New Dibenzofuran- and 7-Nitrodibenzofuran-2-Sulfonylamino Acid Derivatives," *Acta Pharm. Jugosl.*, 1985, 35(1), 15-22.

El-Naggar, A.M. et al., "Synthesis and Biological Activity of Some New Quinoline-8-Sulfonylamino Acid and Dipeptide Derivatives," *Acta Pharm. Jugosl.*, 1983, 33(2), 103-10.

El Naggar, A.M. et al., "Synthesis of Thiophene-2-Sulfony-Amino Acid and Dipeptide Derivatives," *Egypt J. Chem.*, 1981, 23(4), 273-9.

Fricker, Lloyd D. and Solomon, Snyder H., "Purification and Characterization of Enkephalin Convertase, an Enkephalin-Synthesizing Carboxypeptidase," *J. Biol. Cham.*, (1983), 258(18), 10950-5.

Fujita, Tsunehisa, et al., "Free-Radical Polymerization of Maleimide Derivaties in the Presence of Chiral Substances," *J. Macromal. Sci., Chem.*, 1988, A25(3), 327-36.

Hosaka, Toshihiro, et al., "An Efficient Protocol for the Selective Reduction of Benzenesulfonyllaclam to Benzenesulfonyl Cyclic Amine," *Tetrahedron Lett.*, 1997, 38(20), 3535-38.

Huart, Catherine and Ghosez, Leon, "Asymmetric Cyclopentannulation of Cyclic Enones With a Chiral 1,3-Dipole Equivalent." *Angew. Chem.*, 36(6), 1997, 634-36.

Hui, Koon-Sea et al., "Separation of Alkylamino-naphthylenesulfonyl Peptides and Amino Acids by High-Performance Liquid Chromatography. Methods for Measuring melanotropin Inhibiting Factor Breakdown," *J. Chromatogr.*, 1980, 192(2), 341-50.

Ibrahim, T.M.at al., "Synthesis and Antimicrobial Activity of Some New 4-nitrothiophene-2-sulphonyl Amino Acid Derivatives," *Indian J. Heterocycl. Chem.*, 1993, 3(1), 31-36.

Ibrahim, T. M. et al.,"Synthesis and Antimicrobial Activity of Some New 7-Methoxy-4-Methylcoumarin-6-Sulfonylamino Acid Derivatives," *Proc. Indian Natl. Sci. Acad.*, Part A (1994), 60(2), 433-39.

Kozikowski, Alan P., et al., "Alzheimer's Therapy: An Approach to Novel Muscarinic Ligands Based Upon the Naturally Occurring Alkoid Himbacine," *Bioorg. Med. Chem., Lett.*, 2(8), 1992, 797-802.

Malin, D.H. et al., "Subcutaneous Injection of an Analog of Neuropeptide FF Prevents Naloxone-Precipitated Morphine Abstinence Syndrome," *Drug Alcohol Depend.*, (1995), 40(1), 37-42.

Malaska, Michael J. et al., "Simplified Analogs of Himbacine Displaying Potent Binding Affinity for Muscarinic Receptors." *Bioorg. Med. Chem Lett.*, 3(6), 1993, 1247-52.

Maekawa, K. et al., "Pesticides Derived From Amino Acids," *Environ. Qual. Saf.*, Suppl. (1975), 3(Pesticides), 748-53.

Moree, Wilna J. et al., "Synthesis of Peptidosulfinamides and Peptidosulfonamides: Peptidomimetics Containing the Sulfinamide or Sulfonamide Transition-State isostere," *J. Org. Chem.*, 1995, 60(16), 5157-69.

Moree, Wilna J. et al., "Exploitation of Subtilisin BPN' as Catalyst for the Syntheis of Peptides Containing Noncoded Amino Acids, Peptide Mimetics and Peptide Conjugates," *J. Am. Chem. Soc.*, 1997, 119(17), 3942-47.

Moss, William et al., "Ketene S,S-Acetais as 1,3-Dipolarophiles Towards Azides. A New Synthetic Entry Into Cyclic Amino Acids," *Tetrahedron*, (1992), 48(36), 7551-64.

Nagasawa, H.T. et al., "Medium Ring Homologs of Proline as Potential Amino Acid Antimetabolites," *J. Med. Chem.*, 1971, 14(6), 501-08.

Nicolaides et al., "Modified Di- and Tripeptides of the C-Terminal Portion of Oxytocin and Vasopressin as Possible Cognition Activation Agents." *J. Med. Chem.*, 29(6), 1986, 959-71.

Nkunya, M. H.H. and Zwanenburg, B., "Asymmetric Synthesis of α, β-Epoxy Sulfonamides (Oxiranesulfonamides)." *Recl. Trav. Chim. Pays-Bas*, 104 (10), 1985, 253-59.

Otto, A. et al., "Detection of C-Terminal Amidated Amino Acids in Peptides by Combined Proteolysis/El-Mass Spectrometry," *Pept., Proc. Eur. Pept. Symp.*, 20th (1989), Meeting Date 1988, 130-32.

Perrio-Huard, Cecile et al., "Syntheses of Piperidine and Perhydroazepine Derivatives, Precursors of Two Selective Antagonists of Muscarinic $M_2$ Receptors: AF-DX 384 and Its Perhydroazepine Isomer." *J. Chem. Soc.*, 1(24), 1996, 2925-32.

Pravda and Rudinger, *Collect Czech. Cham. Commun.*, 20, (1955), 1, 6. (Beilstein Reg. No. 27462).

Royer, J. and Husson, H. P., "2-Cyano-6-Oxazolopiperidine: A Powerful Tool for the Asymmetric Synthesis of Piperidien Derivatives." *Jannsen Chim. Acta*. 11(2), 1993, 3-8.

Shono, Tatsuya et al., "Electroorganic Chemistry. 81. Anodic Oxidation of Sulfonamides and Amidophosphates," *J. Org. Chem.*, (1984), 49(20). 3711-16.

Stryer, Lubert and Haugland, Richard P., "Energy Transfer. Spectroscopic Ruler," *Proc. Natl. Acad. Sci. U.S.A.*, (1967), 58(2), 719-26.

Takasuka, Mamoru et al., "FTIR Spectral Study of Intramolecular Hydrogen Bonding in Thromboxane $A^2$ Receptor Antagonist S-145 and Related Compounds. 3. Conformation and Activity of S-145 Analogs." *J. Med. Chem.*, (1991), 34(6), 1885-91.

Tochilkin, A. I. and Gracheva, I.N., "8-Methoxy-5-quinolinesulfonyl Chloride, A New Fluorogenic Reagent for the Detection of Amines and Amino Acids," *Biorg. Khim.*, 1990, 16(7), 956-62.

Toyooka, Toshimasa et al., "Evaluation of Benzofurazan Derivatives as Fluorogenic Reagents for Thiols and Amines Using High-Performance Liquid Chromatography," *Analyst*, 1989, 114(10), 1233-40.

Tsuge, Hiro Yasu et al., "Highly Diastereoselective Michael Addition to Optically Active Trifluoromethylated α, β-Unsaturated Sulfonamides Based on Their Hinge-Like Conformation." *Tetrahedron*, 53(3), 1997, 823-38.

Van den Broek, Leon A. G. M. et al., "Asymmetric Diels-Alder Reactions With Sulfines Derived From Proline." *J. Org. Chem.*, 49(10), 1984, 1891-95.

Vedejs, Edwin et al., "Heteroarene-2-sulfonyl Chlorides (BtsCl; ThsCl): Reagents for Nitrogen Protection and >99% Racemization-Free Phenylglycine Activation with $SOCL_2$," *J. Am. Chem. Soc.*, 1996, 118(40), 9796-97.

Wohl and Schaefer, "Und Laesst Des Erhaltene Oel in Der Kaelte Stehen," *Thiele, Chem.Ber.*, 38, (1905), 4157-60.

Zhou, Ye and Sun, Zengpei, "Liquid Chromatographic Evaluation of Chiral Derivatizing Reagents for the Resolution of Amine and Alcohol Enantiomers," *J. Chromatogr.*, (1990), 508(1), 220-04.

Zhou, Ye et al., "Liquid Chromatographic Evaluation of a New Chiral Derivatizing Reagent for Enantiomeric Resolution of Amine and Alcohol Drugs," *J. Liq. Chromalogr.*, (1990), 13(5), 875-85.

Littler, Chemical Abstracts, vol. 126:157674.

Kojima, Chemical Abstracts, vol. 125:316228.

US 5,654,332, 08/1997, Armistead et al. (withdrawn)

* cited by examiner

Promotion of Hair Growth by Neuroimmunophilin Ligands

N-LINKED SULFONAMIDES OF N-HETEROCYCLIC CARBOXYLIC ACIDS OR CARBOXYLIC ACID ISOSTERES

RELATED APPLICATION DATA

This application is a continuation of U.S. patent application Ser. No. 09/791,660, filed Feb. 26, 2001 now abandoned, which is a divisional of U.S. patent application Ser. No. 09/204,236, filed Dec. 3, 1998, which claims benefit of provisional application Ser. No. 60/087,842, filed Jun. 3, 1998.

BACKGROUND OF THE INVENTION

1. Field of the Invention

This invention relates to small molecule compounds and compositions, their preparation and use for treating neurological disorders including physically damaged nerves and neurodegenerative diseases, and for treating alopecia and promoting hair growth.

2. Description of the Prior Art

It has been found that picomolar concentrations of an immunosuppressant such as FK506 and rapamycin stimulate neurite outgrowth in PC12 cells and sensory nervous, namely dorsal root ganglion cells (DRGs). Lyons et al., *Proc. of Natl. Acad. Sci.*, 1994 vol. 91, pp. 3191–3195. In whole animal experiments, FK506 has been shown to stimulate nerve regeneration following facial nerve injury and results in functional recovery in animals with sciatic nerve lesions.

Several neurotrophic factors effecting specific neuronal populations in the central nervous system have been identified. For example, it has been hypothesized that Alzheimer's disease results from a decrease or loss of nerve growth factor (NGF). It has thus been proposed to treat Alzheimer's patients with erogenous nerve growth factor or other neurotrophic proteins such as brain derived nerve factor (BDNF) glial derived nerve factor, ciliary neurotrophic factor, and neurotropin-3 to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressants exhibit a number of potentially serious side effects including nephrotoxicity, such as impairment of glomerular filtration and irreversible interstitial fibrosis (Kopp et al., 1991, J. Am. Soc. Nephrol. 1:162); neurological deficits, such as involuntary tremors, or non-specific cerebral angina such as non-localized headaches (De Groen et al., 1987, N. Engl. J. Med. 317:861); and vascular hypertension with complications resulting therefrom (Kahan et al., 1989 N. Engl. J. Med. 321: 1725).

Accordingly, there is a need for small-molecule compounds which are useful for neurotrophic effects and for treating neurodegenerative disorders.

Hair loss occurs in a variety of situations. These situations include male pattern alopecia, alopecia senilis, alopecia areata, diseases accompanied by basic skin lesions or tumors, and systematic disorders such as nutritional disorders and internal secretion disorders. The mechanisms causing hair loss are very complicated, but in some instances can be attributed to aging, genetic disposition, the activation of male hormones, the loss of blood supply to hair follicles, and scalp abnormalities.

The immunosuppressant drugs FK506, rapamycin and cyclosporin are well known as potent T-cell specific immunosuppressants, and are effective against graft rejection after organ transplantation. It has been reported that topical, but not oral, application of FK506 (Yamamoto et al., J. Invest. Dermatol., 1994, 102, 160–164; Jiang et al., J. Invest. Dermatol. 1995, 104, 523–525) and cyclosporin (Iwabuchi et al., J. Dermatol. Sci. 1995, 9, 64–69) stimulates hair growth in a dose-dependent manner. One form of hair loss, alopecia areata, is known to be associated with autoimmune activities; hence, topically administered immunomodulatory compounds are expected to demonstrate efficacy for treating that type of hair loss. The hair growth stimulating effects of FK506 have been the subject of an international patent filing covering FK506 and structures related thereto for hair growth stimulation (Honbo et al., EP 0 423 714 A2). Honbo et al. discloses the use of relatively large tricyclic compounds, known for their immunosuppressive effects, as hair revitalizing agents.

The hair growth and revitalization effects of FK506 and related agents are disclosed in many U.S. patents (Goulet et al., U.S. Pat. No. 5,258,389; Luly et al., U.S. Pat. No. 5,457,111; Goulet et al., U.S. Pat. No. 5,532,248; Goulet et al., U.S. Pat. No. 5,189,042; and Ok et al., U.S. Pat. No. 5,208,241; Rupprecht et al., U.S. Pat. No. 5,284,840; Organ et al., U.S. Pat. No. 5,284,877). These patents claim FK506 related compounds. Although they do not claim methods of hair revitalization, they disclose the known use of FK506 for effecting hair growth. Similar to FK506 (and the claimed variations in the Honbo et al. patent), the compounds claimed in these patents are relatively large. Further, the cited patents relate to immunomodulatory compounds for use in autoimmune related diseases, for which FK506's efficacy is well known.

Other U.S. patents disclose the use of cyclosporin and related compounds for hair revitalization (Hauer et al., U.S. Pat. No. 5,342,625; Eberle, U.S. Pat. No. 5,284,826; Hewitt et al., U.S. Pat. No. 4,996,193). These patents also relate to compounds useful for treating autoimmune diseases and cite the known use of cyclosporin and related immunosuppressive compounds for hair growth.

However, immunosuppressive compounds by definition suppress the immune system and also exhibit other toxic side effects. Accordingly, there is a need for small molecule compounds which are useful as hair revitalizing is compounds.

SUMMARY OF THE INVENTION

The present invention relates to the surprising discovery that N-heterocyclic sulfonamide compounds containing a carboxylic acid or carboxylic acid isostere moiety may be useful for treating neurodegenerative disorders and for treating alopecia and promoting hair growth. Accordingly, a novel class of sulfonamide derivatives containing an acidic moiety or an isostere thereof attached to the 2-carbon of the N-heterocyclic ring are provided. These compounds stimulate neuronal regeneration and outgrowth and as such are useful for treating neurological disorders and neurodegenerative diseases. These compounds also promote hair growth and as such are useful for treating hair loss disorders. A preferred feature of the compounds of the present invention is that they do not exert any significant immunosuppressive activity and/or are non-immunosuppressive.

A preferred embodiment of this invention is a compound having the formula (I):

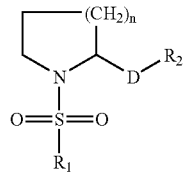

where n is 1–3;

$R_1$ is selected from the group consisting of hydrogen, $C_1$–$C_9$ straight or branched chain alkyl, $C_2$–$C_9$ straight or branched chain alkenyl, aryl, heteroaryl, carbocycle, or heterocycle;

D is a bond, or a $C_1$–$C_{10}$ straight or branched chain alkyl, $C_2$–$C_{10}$ alkenyl or $C_2$–$C_{10}$ alkynyl;

$R_2$ is a carboxylic acid or a carboxylic acid isostere;

wherein said alkyl, alkenyl, alkynyl, aryl, heteroaryl, carbocycle, heterocycle, or carboxylic acid isostere is optionally substituted with one or more substituents selected from $R^3$, where $R^3$ is hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, heteroaryl, carbocycle, heterocycle, or $CO_2R^4$ where $R^4$ is hydrogen or $C_1$–$C_9$ straight or branched chain alkyl or alkenyl;

or a pharmaceutically acceptable salt, ester or solvate thereof;

provided that:

when D is a bond, and $R_2$ is COOH, then $R_1$ cannot be substituted naphthyl;

further provided that:

when D is a bond, and n is 1, and $R_2$ is COOH or $CONHR_3$, then $R_1$ is not hydroxyl, methyl, ethyl, substituted or unsubstituted thioethyl, benzothiazole, substituted benzopyran, substituted benzopyrrole, substituted benzoxazole, substituted 5-membered heterocycle containing two N and one S heteroatoms, or substituted or unsubstituted phenyl, phenylethyl, naphthyl, pyridyl, thienyl, quinoline, tricyclic ring, aminoethyl, or benzyl;

further provided that:

when D is a bond, and n is 2, and $R_2$ is COOH or phenylbutyl ester, then $R_1$ is not substituted phenyl, or a substituted bicyclic ring containing two oxygen heteroatoms.

further provided that:

when D is a bond, and n is 1–2, and $R_2$ is a substituted or unsubstituted carbocyclic or heterocyclic ring structure, then $R_1$ is not substituted or unsubstituted carbocycle or heterocycle, or hydroxy;

further provided that:

when D is a bond, and n is 1–2, and $R_2$ is hydroxy, alkoxy, —$SO_2$(phenyl), $N(R_3)_2$, substituted thio or alkylthio, —NCO, —$PO_3(Me)_2$, or —NCOOC(ethyl)phenyl, then $R_1$ is not naphthalene, ethylene, substituted tricyclic ring, or substituted or unsubstituted phenyl;

further provided that:

when D is $C_1$–$C_3$ alkyl or hexenyl, and $R_2$ is hydroxyl, then $R_1$ is not substituted or unsubstituted phenyl, or benzoimidazole;

further provided that:

when D is methyl, and n is 1, and $R_2$ is cyano or COOH, then R1 is not substituted phenyl;

further provided that:

when D is methyl, and n is 1, and $R_2$ is methoxy or $N(R_3)_2$; then $R_1$ is not methyl, ethyl, phenylethyl, chloro substituted alkyl, substituted oxirane, substituted aziridine wherein one of the carbons is replaced with an oxygen, substituted or unsubstituted propenyl, substituted phenyl, benzyl, or trifluoro substituted $C_2$–$C_3$ alkyl or alkenyl;

further provided that:

when D is ethyl, and n is 2, and $R_2$ is hydroxyl or $N(R_3)_2$, then $R_1$ is not naphthyl;

further provided that:

when D is propyl, and n is 1, and $R_2$ is methoxy, then $R_1$ is not ethylene, cyano substituted ethyl, or triethoxy substituted propyl;

further provided that:

when D is not a bond and at least one of D and $R_2$ contains at least one S or O, then $R_1$ is not methyl or substituted phenyl.

A preferred embodiment of this invention is where $R_2$ is a carbocycle or heterocycle containing any combination of $CH_2$, O, S, or N in any chemically stable oxidation state, where any of the atoms of said ring structure are optionally substituted in one or more positions with $R^3$.

Especially preferred embodiments of this invention are where $R_2$ is selected from the group below:

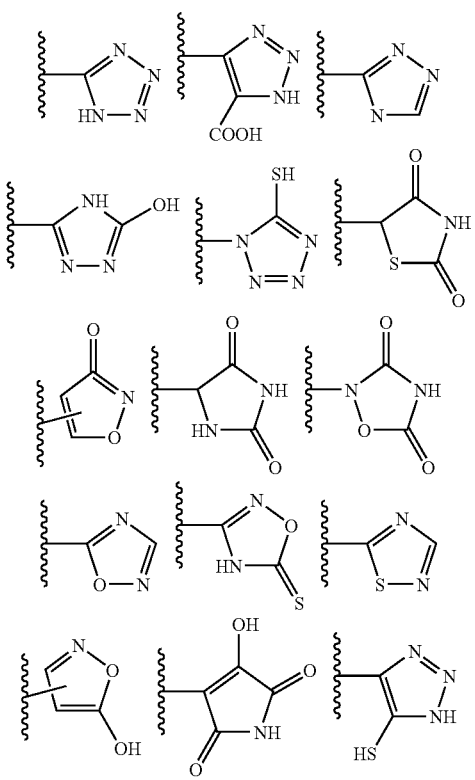

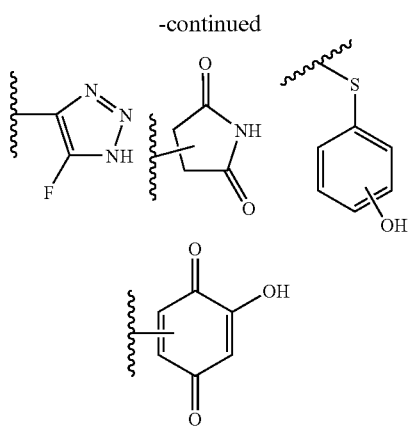

where the atoms of said ring structure may be optionally substituted at one or more positions with $R^3$.

Another preferred embodiment of this invention is where $R_2$ is selected from the group consisting of —COOH, —SO$_3$H, —SO$_2$HNR$^3$, —PO$_2$(R$^3$)$_2$, —CN, —PO$_3$(R$^3$)$_2$, —OR$^3$, —SR$^3$, —NHCOR$^3$, —N(R$^3$)$_2$, —CON(R$^3$)$_2$, —CONH(O)R$^3$, —CONHNHSO$_2$R$^3$, —COHNSO$_2$R$^3$, and —CONR$^3$CN.

Preferred embodiments of this invention are compounds of the formula: (2S)-1-(phenylmethyl)sulfonyl-2-hydroxymethyl pyrrolidine; (2S)-1-(phenylmethyl)sulfonyl-2-pyrrolidinetetrazole; (2S)-1-(phenylmethyl) sulfonyl-2-pyrrolidine carbonitrile; and compounds 1–136.

Another preferred embodiment of this invention is a composition containing: a therapeutically effective amount of a compound of formula (I); a neurotrophic factor different from formula (I); and a pharmaceutically suitable carrier.

Another preferred embodiment of the invention is a method of promoting neuronal regeneration and growth in mammals, comprising administering to a mammal an effective amount of a N-linked sulfonamide of an N-heterocyclic carboxylic acid or carboxylic acid isostere.

Another preferred embodiment of the invention is a method of treating a neurological disorder in an animal, comprising administering to an animal a therapeutically effective amount of a N-linked sulfonamide of an N-heterocyclic carboxylic acid or carboxylic acid isostere to stimulate growth of damaged peripheral nerves or to promote neuronal regeneration.

Yet another preferred embodiment of the invention is a method of preventing neurodegeneration in an animal, comprising administering to an animal an effective amount of an N-linked sulfonamimde of an N-heterocyclic carboxylic acid or carboxylic acid isostere.

Yet another preferred embodiment of the invention is a method of treating alopecia or promoting hair growth in an animal, comprising administering to an animal an effective amount of an N-linked sulfonamide of an N-heterocyclic carboxylic acid or carboxylic acid isostere.

BRIEF DESCRIPTION OF THE DRAWINGS

FIG. 2 shows that less than 3% of the shaved area is covered with new hair growth when the vehicle (control) is administered.

DETAILED DESCRIPTION OF THE INVENTION

Definitions

Figure 1:
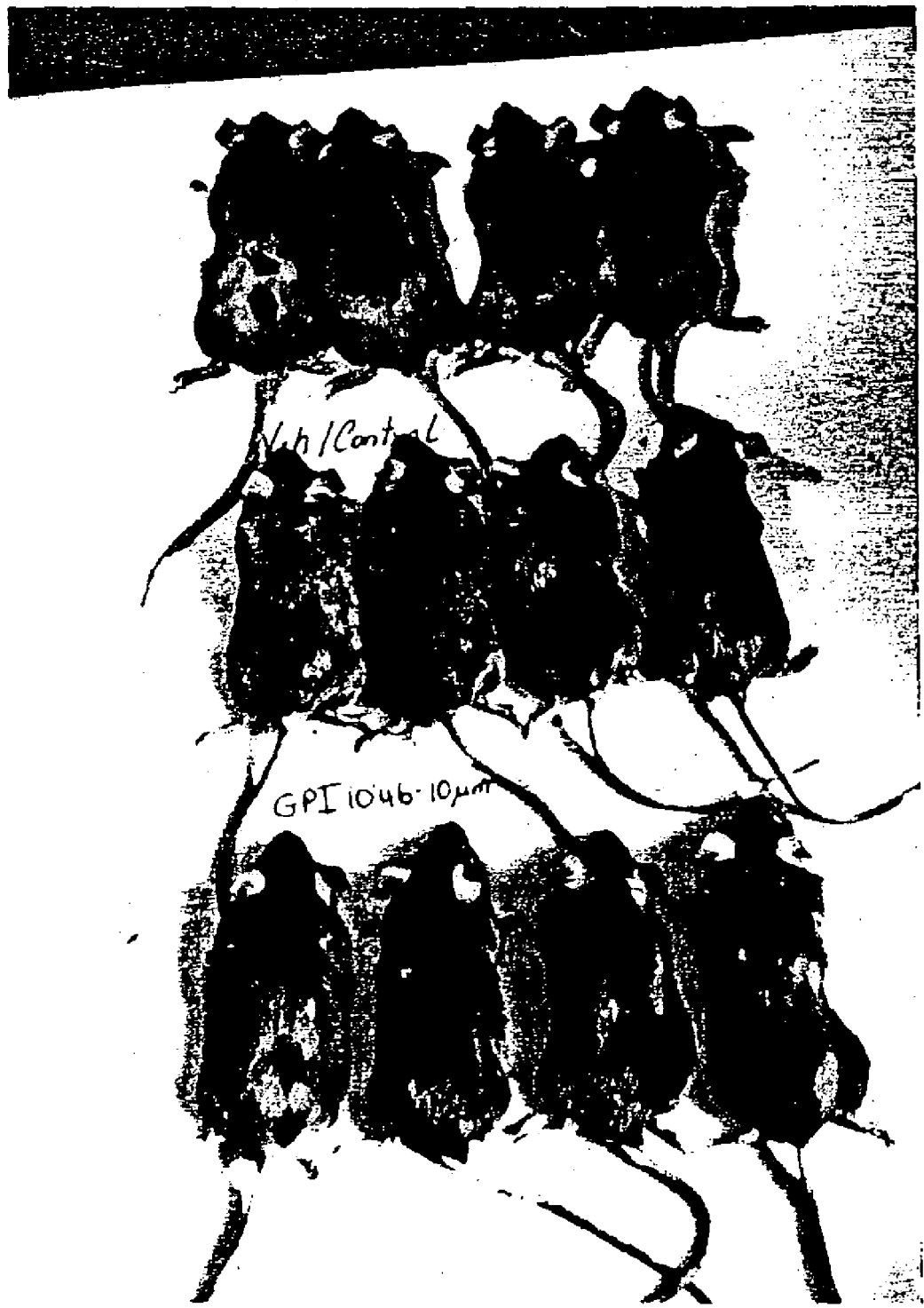
FIG. 1 is a photograph of C57 Black 6 mice before being shaved for the hair regeneration experiment.

"Alkyl" means a branched or unbranched saturated hydrocarbon chain comprising a designated number of carbon atoms. For example, $C_1$–$C_6$ straight or branched alkyl hydrocarbon chain contains 1 to 6 carbon atoms, and includes but is not limited to substituents such as methyl, ethyl, propyl, iso-propyl, butyl, iso-butyl, tert-butyl, n-pentyl, n-hexyl, and the like. It is also contemplated as within the scope of the present invention that "alkyl" may also refer to a hydrocarbon chain wherein any of the carbon atoms of said alkyl are optionally replaced with O, NH, S, or SO$_2$. For example, carbon 2 of n-pentyl can be replaced with O to form propyloxymethyl.

"Alkenyl" means a branched or unbranched unsaturated hydrocarbon chain comprising a designated number of carbon atoms. For example, $C_2$–$C_6$ straight or branched alkenyl hydrocarbon chain contains 2 to 6 carbon atoms having at least one double bond, and includes but is not limited to substituents such as ethenyl, propenyl, iso-propenyl, butenyl, iso-butenyl, tert-butenyl, n-pentenyl, n-hexenyl, and the like. It is also contemplated as within the scope of the present invention that "alkenyl" may also refer to an unsaturated hydrocarbon chain wherein any of the carbon atoms of said alkenyl are optionally replaced with O, NH, S, or SO$_2$. For example, carbon 2 of 4-pentene can be replaced with O to form (2-propene)oxymethyl.

"Alkoxy" means the group —OR wherein R is alkyl as herein defined. Preferably, R is a branched or unbranched saturated hydrocarbon chain containing 1 to 6 carbon atoms.

The term "carbocycle" or refers to an organic cyclic moiety in which the cyclic skeleton is comprised of only carbon atoms whereas the term "heterocycle" refers to an organic cyclic moiety in which the cyclic skeleton contains one or more heteroatoms selected from nitrogen, oxygen, or sulfur and which may or may not include carbon atoms.

Thus, the term "carbocycle" refers to a carbocyclic moiety containing the indicated number of carbon atoms. The term "$C_3$–$C_8$ cycloalkyl", therefore, refers to an organic cyclic substituent in which three to eight carbon atoms form a three, four, five, six, seven, or eight-membered ring, including, for example, a cyclopropyl, cyclobuty;, cyclopentyl, cyclohexyl, cycloheptyl, or cyclooctyl ring. As used herein, "carbocycle" may also refer to two or more cyclic ring systems which are fused to form, for example bicyclic, tricyclic, or other similar bridged substituents (e.g. adamantyl).

"Aryl" refers to an aromatic carbocyclic group having a single ring, for example a phenyl ring; multiple rings, for example biphenyl; or multiple condensed rings in which at least one ring is aromatic, for example naphthyl, 1,2,3,4-tetrahydronaphthyl, anthryl, or phenanthryl, which can be unsubstituted or substituted with one or more other substituents as defined above. The substituents attached to a phenyl ring portion of an aryl moiety in the compounds of Formula (I) may be configured in the ortho-, meta-, or para-orientations.

Examples of typical aryl moieties included in the scope of the present invention may include, but are not limited to, the following:

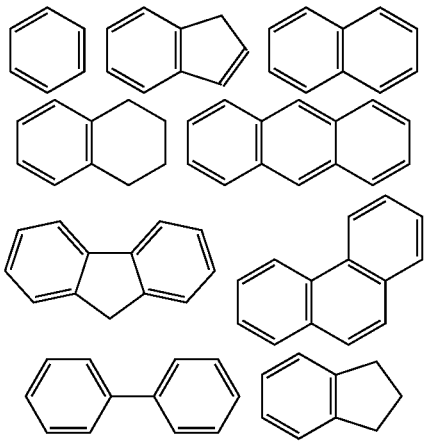

"Aralkyl" refers to alkyl or alkylene (alkenyl) chain which is substituted with aryl, heteroaryl, carbocycle or heterocycle, or alternatively one or more aryl, heteroaryl, carbocycle, or heterocycle(s) which is/are substituted with alkyl or alkenyl, i.e. 'Alkyl/alkylene which is substituted with Ar' or 'Ar which is substituted with alkyl/alkylene'.

"Heterocycle" refers to a saturated, unsaturated, or aromatic carbocyclic group having a single ring, multiple rings, or multiple condensed rings, and having at least one hetero atom such as nitrogen, oxygen, or sulfur within at least one of the rings. "Heteroaryl" refers to a heterocycle in which at least one ring is aromatic. Any of the heterocyclic or heteroaryl groups can be unsubstituted or optionally substituted with one or more groups as defined above. Further, bi- or tri-cyclic heteroaryl moieties may comprise at least one ring which is either completely or partially saturated.

As one skilled in the art will appreciate, such heterocyclic moieties may exist in several isomeric forms, all of which are encompassed by the present invention. For example, a 1,3,5-triazine moiety is isomeric to a 1,2,4-triazine group. Such positional isomers are to be considered within the scope of the present invention. Likewise, the heterocyclic or heteroaryl groups can be bonded to other moieties in the compounds of the present invention. The point(s) of attachment to these other moieties is not to be construed as limiting on the scope of the invention. Thus, by way of example, a pyridyl moiety may be bound to other groups through the 2-, 3-, or 4-position of the pyridyl group. All such configurations are to be construed as within the scope of the present invention.

Examples of heterocyclic or heteroaryl moieties included in the scope of the present invention may include, but are not limited to, the following:

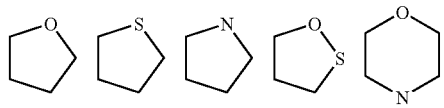

"Halo" means at least one fluoro, chloro, bromo, or iodo moiety.

The term "pharmaceutically acceptable salt, ester, or solvate" refers to salt, ester, or solvates of the subject compounds which possess the desired pharmacological activity and which are neither biologically nor otherwise undesirable. The salt, ester, or solvates can be formed with inorganic or organic acids such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, gluconate, glycerophosphate, hemisulfate, heptanoate, hexanoate, hydrochloride hydrobromide, hydroiodide, 2-hydroxyethanesulfonate, lactate, maleate, methanesulfonate, naphthylate, 2-naphthalene-sulfonate, nicotinate, oxalate, sulfate, thiocyanate, tosylate and undecanoate. Base salt, ester, or solvates include ammonium salts, alkali metal salts such as lithium, sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quaternized with such agents as: 1) lower alkyl halides, such as methyl, ethyl, propyl, and butyl chloride, bromides and iodides; 2) dialkyl sulfates like dimethyl, diethyl, dibutyl and diamyl sulfates; 3) long chain alkyls such as decyl, lauryl, myristyl and stearyl substituted with one or more halide such as chloride, bromide and iodide; and 4) aryl or arylalkyl halides like benzyl and phenethyl bromide and others.

The compounds of this invention may possess at least one asymmetric center and thus can be produced as mixtures of stereoisomers or as individual enantiomers or diastereomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention. The S-stereoisomer at atom 1 of formula I is a most preferred embodiment of the invention.

"Stereoisomers" are isomers that differ only in the way the atoms are arranged in space.

"Isomers" are different compounds that have the same molecular formula and includes cyclic isomers such as (iso)indole and other isomeric forms of cyclic moieties.

"Enantiomers" are a pair of stereoisomers that are non-superimposable mirror images of each other.

"Diastereoisomers" are stereoisomers which are not mirror images of each other.

"Racemic mixture" means a mixture containing equal parts of individual enantiomers. "Non-racemic mixture" is a mixture containing unequal parts of individual enantiomers or stereoisomers.

"Isosteres" are different compounds that have different molecular formulae but exhibit the same or similar properties. For example, tetrazole is an isostere of carboxylic acid because it mimics the properties of carboxylic acid even though they both have very different molecular formulae. Tetrazole is one of many possible isosteric replacements for carboxylic acid. Other carboxylic acid isosteres contemplated by the present invention include —COOH, —SO$_3$H, —SO$_2$HNR$^3$, —PO$_2$(R$^1$)$_2$, —CN, —PO$_3$(R$^3$)$_2$, —OR$^3$, —SR$^3$, —NHCOR$^3$, —N(R$^3$)$_2$, —CON(R$^3$)$_2$, —CONH(O)R$^3$, —CONHNHSO$_2$R$^3$, —COHNSO$_2$R$^3$, and —CONR$^3$CN.

In addition, carboxylic acid isosteres can include 5–7 membered carbocycles or heterocycles containing any combination of CH$_2$, O, S, or N in any chemically stable oxidation state, where any of the atoms of said ring structure are optionally substituted in one or more positions. The following structures are non-limiting examples of preferred carbocyclic and heterocyclic isosteres contemplated by this invention.

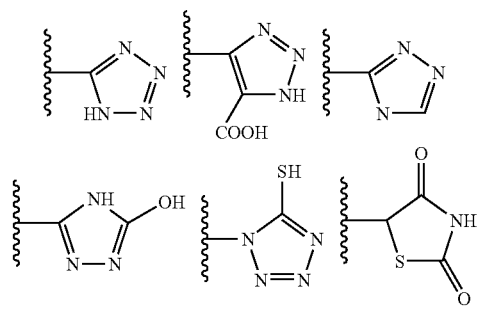

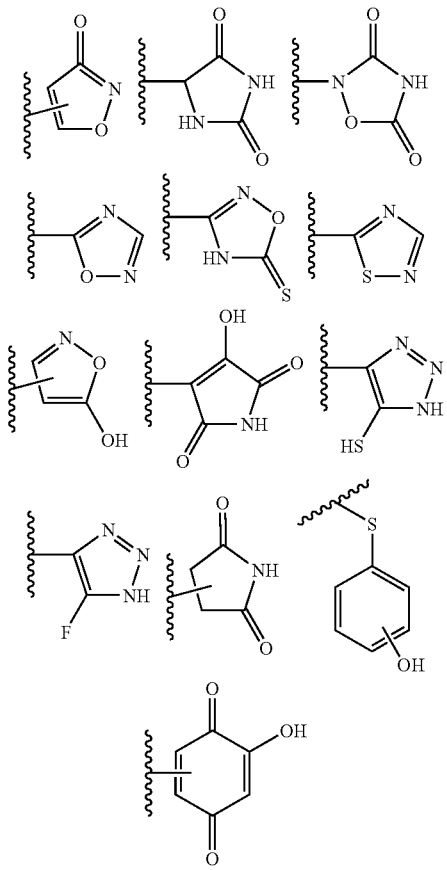

where the atoms of said ring structure may be optionally substituted at one or more positions with R$^3$. The present invention contemplates that when chemical substituents are added to a carboxylic isostere then the inventive compound retains the properties of a carboxylic isostere. The present invention contemplates that when a carboxylic isostere is optionally substituted with one or more moieties selected from R$^3$, then the substitution can not eliminate the carboxylic acid isosteric properties of the inventive compound. The present invention contemplates that the placement of one or more R$^3$ substituents upon a carbocyclic or heterocyclic carboxylic acid isostere shall not be at an atom(s) which maintains or is integral to the carboxylic acid isosteric properties of the inventive compound if such a substituent(s) would destroy the carboxylic acid isosteric properties of the inventive compound.

Other carboxylic acid isosteres not specifically exemplified or described in this specification are also contemplated by the present invention.

The term "preventing neurodegeneration" as used herein includes the ability to inhibit or prevent neurodegeneration in patients newly diagnosed as having a neurodegenerative disease, or at risk of developing a new degenerative disease and for inhibiting or preventing further neurodegeneration in patients who are already suffering from or have symptoms of a neurodegenerative disease when the compounds are given concurrently.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

The system used in naming the compounds of the present invention is shown below, using a compound of formula I as an example.

A compound of the present invention, especially formula I, wherein n is 1, D is a bond, $R_1$ is phenylmethyl, and $R_2$ is —CN, is named (2S)-1-(phenylmethyl) sulfonyl-2-pyrrolidine carbonitrile.

"Alopecia" refers to deficient hair growth and partial or complete loss of hair, including without limitation androgenic alopecia (male pattern baldness), toxic alopecia, alopecia senilis, alopecia areata, alopecia pelada and trichotillomania. Alopecia results when the pilar cycle is disturbed. The most frequent phenomenon is a shortening of the hair growth or anagen phase due to cessation of cell proliferation. This results in an early onset of the catagen phase, and consequently a large number of hairs in the telogen phase during which the follicles are detached from the dermal papillae, and the hairs fall out. Alopecia has a number of etiologies, including genetic factors, aging, local and systemic diseases, febrile conditions, mental stresses, hormonal problems, and secondary effects of drugs.

"Pilar cycle" refers to the life cycle of hair follicles, and includes three phases:

(1) the anagen phase, the period of active hair growth which, insofar as scalp hair is concerned, lasts about three to five years;

(2) the catagen phase, the period when growth stops and the follicle atrophies which, insofar as scalp hair is concerned, lasts about one to two weeks; and (3) the telogen phase, the rest period when hair progressively separates and finally falls out which, insofar as scalp hair is concerned, lasts about three to four months.

Normally 80 to 90 percent of the follicles are in the anagen phase, less than 1 percent being in the catagen phase, and the rest being in the telogen phase. In the telogen phase, hair is uniform in diameter with a slightly bulbous, non-pigmented root. By contrast, in the anagen phase, hair has a large colored bulb at its root.

"Promoting hair growth" refers to maintaining, inducing, stimulating, accelerating, or revitalizing the germination of hair.

"Treating alopecia" refers to:

(i) preventing alopecia in an animal which may be predisposed to alopecia; and/or (ii) inhibiting, retarding or reducing alopecia; and/or (iii) promoting hair growth; and/or (iv) prolonging the anagen phase of the hair cycle; and/or (v) converting vellus hair to growth as terminal hair. Terminal hair is coarse, pigmented, long hair in which the bulb of the hair follicle is seated deep in the dermis. Vellus hair, on the other hand, is fine, thin, non-pigmented short hair in which the hair bulb is located superficially in the dermis. As alopecia progresses, the hairs change from the terminal to the vellus type.

The term "neurotrophic" as used herein includes without limitation the ability to stimulate neuronal regeneration or growth and/or the ability to prevent or treat neurodegeneration.

The term "non-immunosuppressive" refers to the inability of the compounds of the present invention to trigger an immune response when compared to a control such as FK506 ro cyclosporin A. Assays for determining immunosuppression are well known to those of ordinary skill in the art. Specific non-limiting examples of well known assays include PER and OKT3 assays wherein mitogens are used to stimulate proliferation of human peripheral blood lymphocytes (PBC). Compounds added to such assay systems are evaluated for their ability to inhibit such proliferation.

Compounds of the Invention

The present invention relates to the surprising discovery that N-linked sulfonamides of N-heterocyclic carboxylic acid or carboxylic acid isostere compounds are neurotrophic and are able to treat alopecia. Accordingly, a novel class of compounds are provided. A preferred feature of the compounds of the present invention is that they do not exert any significant immunosuppressive activity.

Preferred compounds of the present invention contain carboxylic acid moieties and other isosteric replacements for carboxylic acid moieties, of which several examples are specified herein. Other isosteric replacements for carboxylic acid moieties, known to those skilled in the art of medicinal chemistry, are within the scope of the invention if not otherwise specified.

The neurotrophic compounds of this invention can be periodically administered to a patient undergoing treatment for neurological disorders or for other reasons in which it is desirable to stimulate neuronal regeneration and growth, such as in various peripheral neuropathic and neurological disorders relating to neurodegeneration. The compounds of this invention can also be administered to mammals other than humans for treatment of various mammalian neurological disorders.

The novel compounds of the present invention possess an excellent degree of neurotrophic activity. This activity is useful in the stimulation of damaged neurons, the promotion of neuronal regeneration, the prevention of neurodegeneration, and in the treatment of several neurological disorders known to be associated with neuronal degeneration and peripheral neuropathies. The neurological disorders that may be treated include but are not limited to: trigeminal neuralgia, glossopharyngeal neuralgia, Bell's Palsy, myasthenia gravis, muscular dystrophy, amyotrophic lateral sclerosis, progressive muscular atrophy, progressive bulbar inherited muscular atrophy, herniated, ruptured or prolapsed invertebrate disk syndromes, cervical spondylosis, plexus disorders, thoracic outlet destruction syndromes, peripheral neuropathic such as those caused by lead, dapsone, ticks, prophyria, or Gullain-Barré syndrome, Alzheimer's disease, and Parkinson's disease.

The above discussion relating to the utility and administration of the compounds of the present invention also applies to the pharmaceutical compositions of the present invention.

The term "pharmaceutically acceptable carrier" as used herein refers to any carrier, diluent, excipient, suspending agent, lubricating agent, adjuvant, vehicle, delivery system, emulsifier, disintegrant, absorbant, preservative, surfactant, colorant, flavorant, or sweetener.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

For oral administration, the compounds of the present invention may be provided in any suitable dosage form known in the art. For example, the compositions may be incorporated into tablets, powders, granules, beads, chewable lozenges, capsules, liquids, aqueous suspensions or solutions, or similar dosage forms, using conventional equipment and techniques known in the art. Tablet dosage forms are preferred. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient.

When preparing dosage form incorporating the compositions of the invention, the compounds may also be blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethylcellulose and sodium starch glycolate; suspending agents, such as povidone, polyvinyl alcohol, and the like; absorbants, such as silicon dioxide; preservatives, such as methylparaben, propylparaben, and sodium benzoate; surfactants, such as sodium lauryl sulfate, polysorbate 80, and the like; colorants such as F.D.& C. dyes and lakes; flavorants; and sweeteners.

Compositions and methods of the invention also may utilize controlled release technology. Thus, for example, the inventive compounds may be incorporated into a hydrophobic polymer matrix for controlled release over a period of days. Such controlled release films are well known to the art. Particularly preferred are transdermal delivery systems. Other examples of polymers commonly employed for this purpose that may be used in the present invention include nondegradable ethylene-vinyl acetate copolymer and degradable lactic acid-glycolic acid copolymers which may be used externally or internally. Certain hydrogels such as poly(hydroxyethylmethacrylate) or poly(vinylalcohol) also may be useful, but for shorter release cycles then the other polymer releases systems, such as those mentioned above.

To be effective therapeutically as central nervous system targets, the compounds of the present invention should readily penetrate the blood-brain barrier when, peripherally administered. Compounds which cannot penetrate the blood-brain barrier can be effectively administered by an intraventricular route or other appropriate delivery system suitable for administration to the brain.

The compounds of the present invention may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil may be employed including synthetic mono- or di-glycerides. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

The compounds of this invention may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. Suitable topical formulations are readily prepared for each of these areas.

For topical application to the eye, or ophthalmic use, the compounds can be formulated as micronized suspensions in isotonic, pH adjusted sterile saline, or, preferably, as solutions in isotonic, pH adjusted sterile saline, either with or without a preservative such as benzylalkonium chloride. Alternatively for the ophthalmic uses the compounds may be formulated in an ointment such as petrolatum.

For topical application to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration. Typically, in vitro dosage-effect results provide useful guidance on the proper doses for patient administration. Studies in animal models are also helpful. The considerations for determining the proper dose levels are well known in the art.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

To effectively treat alopecia or promote hair growth, the compounds used in the inventive methods and pharmaceutical compositions must readily affect the targeted areas. For these purposes, the compounds are preferably administered topically to the skin.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

The compounds can be administered for treatment of hair loss with other hair revitalizing agents. Specific dose levels for the other hair revitalizing agents will depend upon the factors previously stated and the effectiveness of the drug combination.

Other routes of administration known in the pharmaceutical art are also contemplated by this invention.

Specific embodiments of the inventive compounds are presented in Table I. The present invention contemplates employing the compounds of Table I, below, for use in compositions and methods to prevent and/or treat a neurological disorder in an animal, and for use in compositions and methods to treat alopecia and promote hair growth in an animal, and all other uses suggested in this specification.

TABLE I

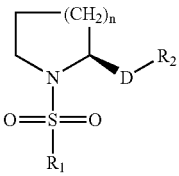

| No. | n | D | R2 | R1 |
|---|---|---|---|---|
| 1 | 1 | bond | COOH | Benzyl |
| 2 | 1 | bond | COOH | α-MethylBenzyl |
| 3 | 1 | bond | COOH | 4-MethylBenzyl |
| 4 | 1 | bond | Tetrazole | Benzyl |
| 5 | 1 | bond | $SO_3H$ | α-MethylBenzyl |
| 6 | 1 | $CH_2$ | COOH | 4-MethylBenzyl |
| 7 | 1 | bond | $SO_2HNMe$ | Benzyl |
| 8 | 1 | bond | CN | α-MethylBenzyl |
| 9 | 1 | bond | $PO_3H_2$ | 4-MethylBenzyl |
| 10 | 2 | bond | COOH | Benzyl |
| 11 | 2 | bond | COOH | α-MethylBenzyl |
| 12 | 2 | bond | COOH | 4-MethylBenzyl |
| 13 | 2 | bond | COOH | 3,4,5-trimethoxyphenyl |
| 14 | 2 | bond | COOH | Cyclohexyl |
| 15 | 2 | bond | $PO_2HEt$ | i-propyl |
| 16 | 2 | bond | $PO_3HPropyl$ | ethyl |
| 17 | 2 | bond | $PO_3(Et)_2$ | Methyl |
| 18 | 2 | bond | OMe | tert-butyl |
| 19 | 2 | bond | OEt | n-pentyl |
| 20 | 2 | bond | OPropyl | n-hexyl |
| 21 | 1 | bond | OButyl | Cyclohexyl |
| 22 | 1 | bond | OPentyl | cyclopentyl |
| 23 | 1 | bond | OHexyl | n-heptyl |
| 24 | 1 | bond | SMe | n-octyl |
| 25 | 1 | bond | SEt | n-nonyl |
| 26 | 2 | bond | SPropyl | 2-indolyl |
| 27 | 2 | bond | SButyl | 2-furyl |
| 28 | 2 | bond | NHCOMe | 2-thiazolyl |
| 29 | 2 | bond | NRCOEt | 2-thienyl |
| 30 | 1 | $CH_2$ | $N(Me)_2$ | 2-pyridyl |
| 31 | 1 | $(CH_2)_2$ | N(Me)Et | benzyl |
| 32 | 1 | $(CH_2)_3$ | $CON(Me)_2$ | benzyl |
| 33 | 1 | $(CH_2)_4$ | CONHMe | benzyl |
| 34 | 1 | $(CH_2)_5$ | CONHEt | benzyl |
| 35 | 1 | $(CH_2)_6$ | CONHPropyl | 1,1-dimethylpropyl |
| 36 | 1 | bond | CONH(O)Me | Benzyl |
| 37 | 1 | bond | CONR(O)Et | α-Methylphenyl |
| 38 | 1 | bond | CONH(O)Propyl | 4-Methylphenyl |
| 39 | 2 | bond | COOH | Benzyl |
| 40 | 2 | bond | COOH | α-Methylphenyl |

TABLE I-continued

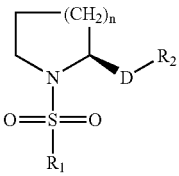

| No. | n | D | R2 | R1 |
|---|---|---|---|---|
| 41 | 2 | bond | COOH | 4-Methylphenyl |
| 42 | 1 | $CH_2$ | COOH | benzyl |
| 43 | 1 | $(CH_2)_2$ | COOH | benzyl |
| 44 | 1 | $(CH_2)_3$ | COOH | benzyl |
| 45 | 1 | $(CH_2)_4$ | COOH | benzyl |
| 46 | 1 | $(CH_2)_5$ | COOH | benzyl |
| 47 | 1 | $(CH_2)_6$ | COOH | benzyl |
| 48 | 1 | $(CH_2)_7$ | COOH | benzyl |
| 49 | 1 | $(CH_2)_8$ | COOH | benzyl |
| 50 | 1 | $(CH_2)_9$ | COOH | benzyl |
| 51 | 1 | $(CH_2)_{10}$ | COOH | benzyl |
| 52 | 1 | $C_2H_2$ | COOH | benzyl |
| 53 | 1 | 2-OH,Et | COOH | benzyl |
| 54 | 1 | 2butylene | COOH | benzyl |
| 55 | 1 | i-Pro | COOH | benzyl |
| 56 | 1 | tert-Bu | COOH | benzyl |
| 57 | 1 | 2-nitro Hexyl | COOH | benzyl |
| 53 | 3 | $(CH_2)_2$ | CN | benzyl |
| 59 | 1 | $(CH_2)_3$ | CN | benzyl |
| 60 | 3 | bond | $CONHNHSO_2Me$ | Benzyl |
| 61 | 3 | bond | $CONHNHSO_2Et$ | α-Methylphenyl |
| 62 | 3 | bond | $CONHSO_2Me$ | 4-Methylphenyl |
| 63 | 2 | bond | $CONHNHSO_2Et$ | Phenyl |
| 64 | 2 | bond | CON(Me)CN | α-Methylphenyl |
| 65 | 2 | bond | CON(Et)CN | 4-Methylphenyl |
| 66 | 1 | $(CH_2)_2$ | COOH | methyl |
| 67 | 1 | $(CH_2)_3$ | COOH | ethyl |
| 68 | 1 | $(CH_2)_4$ | COOH | n-propyl |
| 69 | 1 | $(CH_2)_5$ | COOH | t-butyl |
| 70 | 1 | $(CH_2)_6$ | COOH | Pentyl |
| 71 | 1 | $(CH_2)_7$ | COOH | Hexyl |
| 72 | 1 | $(CH_2)_8$ | COOH | Septyl |
| 73 | 1 | $(CH_2)_9$ | COOH | Octyl |
| 74 | 1 | $(CH_2)_{10}$ | COOH | Nonyl |
| 75 | 1 | $C_2H_2$ | COOH | Cyclohexyl |
| 76 | 1 | bond | 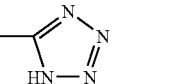 | benzyl |
| 77 | 1 | bond | 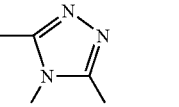 | benzyl |
| 78 | 1 | bond | 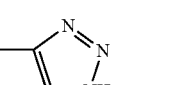 | benzyl |
| 79 | 1 | bond | 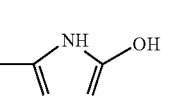 | benzyl |

TABLE I-continued

![structure: pyrrolidine with (CH2)n, N-SO2-R1, and CHR2-D substituent]

| No. | n | D | R2 | R1 |
|---|---|---|---|---|
| 80 | 1 | bond | 1H-tetrazol-5-yl-SH (N-linked) | benzyl |
| 81 | 1 | bond | 2,4-dioxothiazolidin-5-yl | benzyl |
| 82 | 1 | bond | 3-hydroxyisoxazol-4-yl | benzyl |
| 83 | 1 | bond | 2,5-dioxoimidazolidin-4-yl (hydantoinyl) | benzyl |
| 84 | 1 | bond | 5-hydroxyisoxazol-3-yl | benzyl |
| 85 | 1 | bond | 3-hydroxy-2,5-dioxo-2,5-dihydro-1H-pyrrol-4-yl | benzyl |
| 86 | 1 | bond | 5-mercapto-1H-1,2,3-triazol-4-yl | benzyl |
| 87 | 1 | bond | 5-fluoro-1H-1,2,3-triazol-4-yl | benzyl |

TABLE I-continued

![structure: pyrrolidine with (CH2)n, N-SO2-R1, and CHR2-D substituent]

| No. | n | D | R2 | R1 |
|---|---|---|---|---|
| 88 | 1 | bond | 3,5-dioxo-1,2,4-oxadiazolidin-2-yl | benzyl |
| 89 | 1 | bond | 3-ethyl-1,2,4-oxadiazol-5-yl | benzyl |
| 90 | 1 | bond | 5-thioxo-4,5-dihydro-1,2,4-oxadiazol-3-yl | benzyl |
| 91 | 1 | bond | 3-methyl-1,2,4-thiadiazol-5-yl | benzyl |
| 92 | 1 | bond | 2,5-dioxopyrrolidin-3-yl | benzyl |
| 93 | 1 | bond | (2-hydroxyphenyl)thio (S-linked) | benzyl |
| 94 | 1 | bond | 3-hydroxy-2,5-dioxocyclohexa-3,6-dien-1-yl (hydroxybenzoquinonyl) | benzyl |
| 95 | 1 | bond | CH$_2$OH | benzyl |
| 96 | 1 | bond | CONH$_2$ | benzyl |
| 97 | 1 | bond | CN | benzyl |

Additional claimed or comparative carboxylic acids and isosteres of N-heterocyclic compounds which also show the remarkable neurotrophic and hair growth effects of the present invention are shown below in Table II:

TABLE II

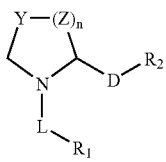

| Cpd | n | D | R$_2$ | L | R$_1$ |
|---|---|---|---|---|---|
| A | 1 | bond | COOH | SO$_2$ | Benzyl |
| B | 1 | bond | CONH$_2$ | SO$_2$ | Benzyl |
| C | 1 | bond | —CN | SO$_2$ | Benzyl |
| D | 1 | bond | tetrazole | SO$_2$ | Benzyl |
| E | 1 | CH$_2$ | —OH | SO$_2$ | Benzyl |
| F | 1 | bond | COOH | 1,2-dioxoethyl | 1,1-dimethylpropyl |
| G | 2 | bond | COOH | 1,2-dioxoethyl | 1,1-dimethylpropyl |
| H | 1 | CH$_2$ | OH | 1,2-dioxoethyl | 1,1-dimethylpropyl |
| I | 1 | bond | tetrazole | 1,2-dioxoethyl | 1,1-dimethylpropyl |
| J | 1 | bond | —CN | 1,2-dioxoethyl | 1,1-dimethylpropyl |
| K | 2 | bond | CONH$_2$ | 1,2-dioxoethyl | 1,1-dimethylpropyl |
| L | 1 | bond | COOH | 1,2-dioxoethyl | 1,1-dimethylpropyl |
| M | 1 | bond | COOH | 1,2-dioxoethyl | 1,1-dimethylpropyl | where Y and Z are both carbon for compounds A–K,
where Z is S for compound H or
where Y is S for compound I.

Pharmaceutical Compositions of the Present Invention

The present invention relates to a pharmaceutical composition comprising:
 (i) an effective amount of an N-linked sulfonamide of N-heterocyclic-carboxylic acid or carboxylic acid isostere compound; and
 (ii) a pharmaceutically acceptable carrier.

The present invention also relates to a pharmaceutical composition comprising:
 (i) an effective amount of an N-linked sulfonamide of N-heterocyclic carboxylic acid or carboxylic acid isostere compound for treating neurodegenerative diseases, neurological disorders, and nerve damage, or promoting nerve growth in an animal; and
 (ii) a pharmaceutically acceptable carrier.

The present invention also relates to a pharmaceutical composition comprising:
 (i) an effective amount of an N-linked sulfonamide of N-heterocyclic carboxylic acid or carboxylic acid isostere compound for treating alopecia or promoting hair growth in an animal; and
 (ii) a pharmaceutically acceptable carrier.

Neurotrophic compounds can be administered with other neurotrophic agents such as neurotrophic growth factor, brain derived growth factor, glial derived growth factor, cilial neurotrophic factor, insulin growth factor and active truncated derivatives thereof, acidic fibroblast growth factor, basic fibroblast growth factor, platelet-derived growth factors, neurotropin-3 and neurotropin 4/5. The dosage level of other neurotrophic drugs will depend upon the factors previously stated and the neurotrophic effectiveness of the drug combination.

Methods of the Present Invention

The present invention relates to the use of any of the compounds seen in Table I and II and other compounds embodied herein, in the preparation of a medicament for the treatment of a disease such as peripheral neuropathy caused by physical injury or disease state, physical damage to the brain, physical damage to the spinal cord, stroke associated with brain damage, Alzheimer's Disease, Parkinson's Disease, and amyotrophic lateral sclerosis. The present invention also relates to the use of carboxylic acid and carboxylic acid isostere compounds for treating the above-mentioned neuropathies, neurological disorders, and neurological damage.

The present invention also relates to a method for treating alopecia or promoting hair growth in an animal, which comprises administering to said animal an effective amount of an N-linked sulfonamide of an N-heterocyclic carboxylic acid or carboxylic acid isostere. The present invention also relates to using the inventive compounds and compositions in the preparation of a medicament for the treatment of alopecia or promoting hair growth in an animal.

The inventive method is particularly useful for treating male pattern alopecia, alopecia senilis, alopecia areata, alopecia resulting from skin lesions or tumors, alopecia resulting from cancer therapy such as chemotherapy and radiation, and alopecia resulting from systematic disorders such as nutritional disorders and internal secretion disorders.

It is understood, however, that a specific dose level for any particular patient will depend upon a variety of factors including the activity of the specific compound employed, the age, body weight, general health, sex, diet, time of administration, rate of excretion, drug combination, and the severity of the particular disease or disorder being treated and form of administration.

MPTP Model of Parkinson's Disease in Mice

MPTP lesioning of dopaminergic neurons in mice is used as an animal model of Parkinson's Disease. Four week old male CD1 white mice are dosed i.p. with 30 mg/kg of MPTP for 5 days. Test compounds (4 mg/kg), or vehicle, are administered s.c. along with the MPTP for 5 days, as well as for an additional 5 days following cessation of MPTP treatment. At 18 days following MPTP treatment, the animals are sacrificed and the striata dissected and perfusion-fixed. Immunostaining is performed on saggital and coronal brain sections using anti-tyrosine hydroxylase 1 g to quantitate survival and recovery of dopaminergic neurons. In animals treated with MPTP and vehicle, a substantial loss of functional dopaminergic terminals is observed as compared to non-lesioned animals. Lesioned animals receiving test compounds show a significant recovery of TH-stained dopaminergic neurons. This model presents quantitation for the recovery of TH-positive dopaminergic neurons in the striatum of animals receiving the compounds of the present invention. Table III presents the percent recovery of dopaminergic neurons in the first (concurrent dosing) paradigm in animals receiving Compound 1, (2S)-1-[(phenylmethyl)sulfonyl]-2-pyrrolidinecarboxylic acid as well related compounds of the present invention.

Table III, below, shows the remarkable neuroregenerative effects of carboxylic acid or carboxylic acid isostere related compounds illustrating the neurotrophic capability of carboxylic acid isosteres as a class showing that lesioned animals receiving the carboxylic acid or carboxylic acid isostere compounds provide a remarkable recovery of TH-stained dopaminergic neurons.

TABLE III

MPTP Neurodegenerative Model

|  | % Recovery |
| --- | --- |
| Compound A | 24.4% |
| Cmpds B–E | ND |
| Compound F | 26.7% |
| Compound G | ND |
| Compound H | 23.2% |
| Compound I | 19.6% |
| Compound J | 34.1% |
| Compound K | 46.5% |
| Compound L | 14.0% |
| Compound M | ND |

Percent striatal innervation density was quantitated is in brain sections with an anti-tyrosine hydroxylase immunoglobulin, which is indicative of functional dopaminergic neurons. The striatal innervation density of 23% for animals pretreated with only a vehicle and administered a vehicle orally during treatment, is indicative of normal non-lesioned striatal tissue. Striatal innervation density is reduced to 5% for animals pretreated with MPTP and administered a vehicle orally during treatment, and is indicative of MPTP-induced lesioning. Surprisingly, striatal innervation density is increased 8–13% for animals pretreated with MPTP and administered 0.4 mg/kg of compound orally during treatment, indicating substantial neuronal regeneration after induction of MPTP-derived lesions.

In Vivo Hair Generation Test with C57 Black 6 Mice

Figure 2:
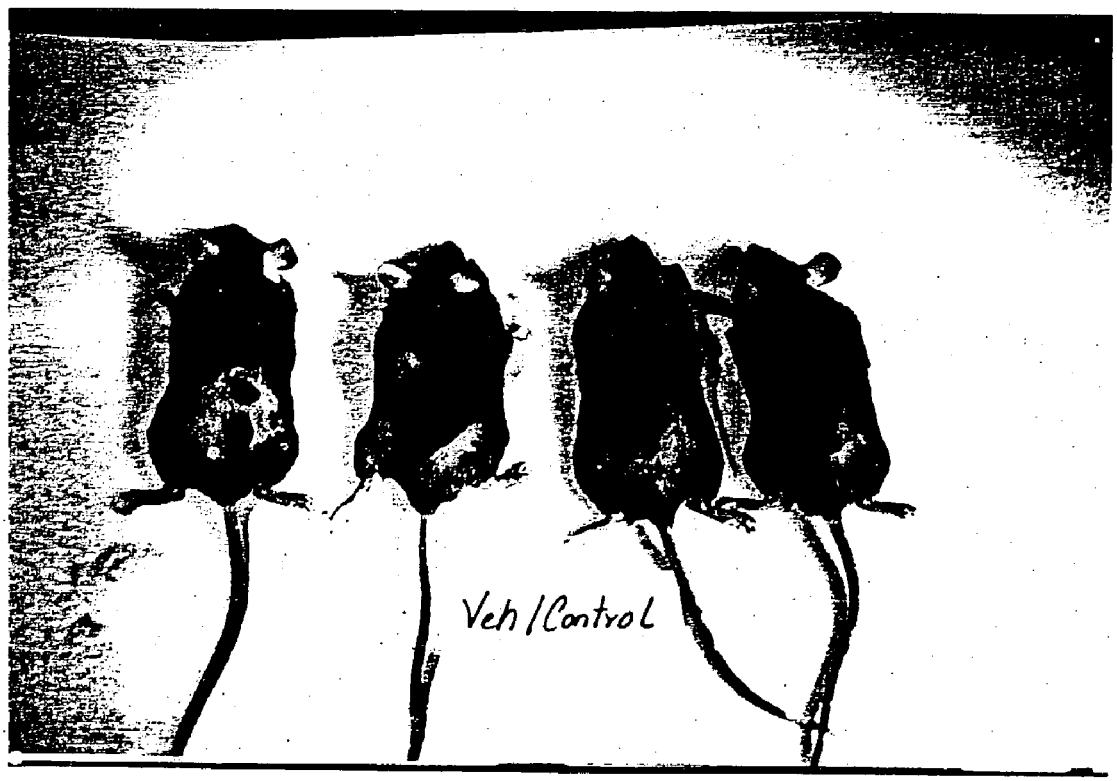
FIG. 2 is a photograph of mice treated with a vehicle after six weeks.

C57 black 6 mice are used to demonstrate the hair revitalizing properties of the ureas and carbamates of N-heterocyclic carboxylic acids or carboxylic acid isosteres. Referring now to FIGS. 1 and 2 of the drawings, C57 black 6 mice, approximately 7 weeks old, had an area of about 2 inches by 2 inches on their hindquarters shaved to remove all existing hair. Care was taken not to nick or cause abrasion to the underlaying dermal layers. The animals were in anagen growth phase, as indicated by the pinkish color of the skin. Referring now to FIG. 2, four animals per group were treated by topical administration with 20% propylene glycol vehicle (FIG. 2), or related compounds dissolved in the vehicle. The animals were treated Faith vehicle or N-heterocyclic carboxylic acids or isosteres every 48 hours (3 applications total over the course of 5 days) and the hair growth was allowed to proceed for 6 weeks. Hair growth was quantitated by the percent of shaved area covered by new hair growth during this time period.

FIG. 2 shows that animals treated with vehicle exhibited only a small amount of hair growth in patches or tufts, with less than 3% of the shaved area covered with new growth.

Figure 3:
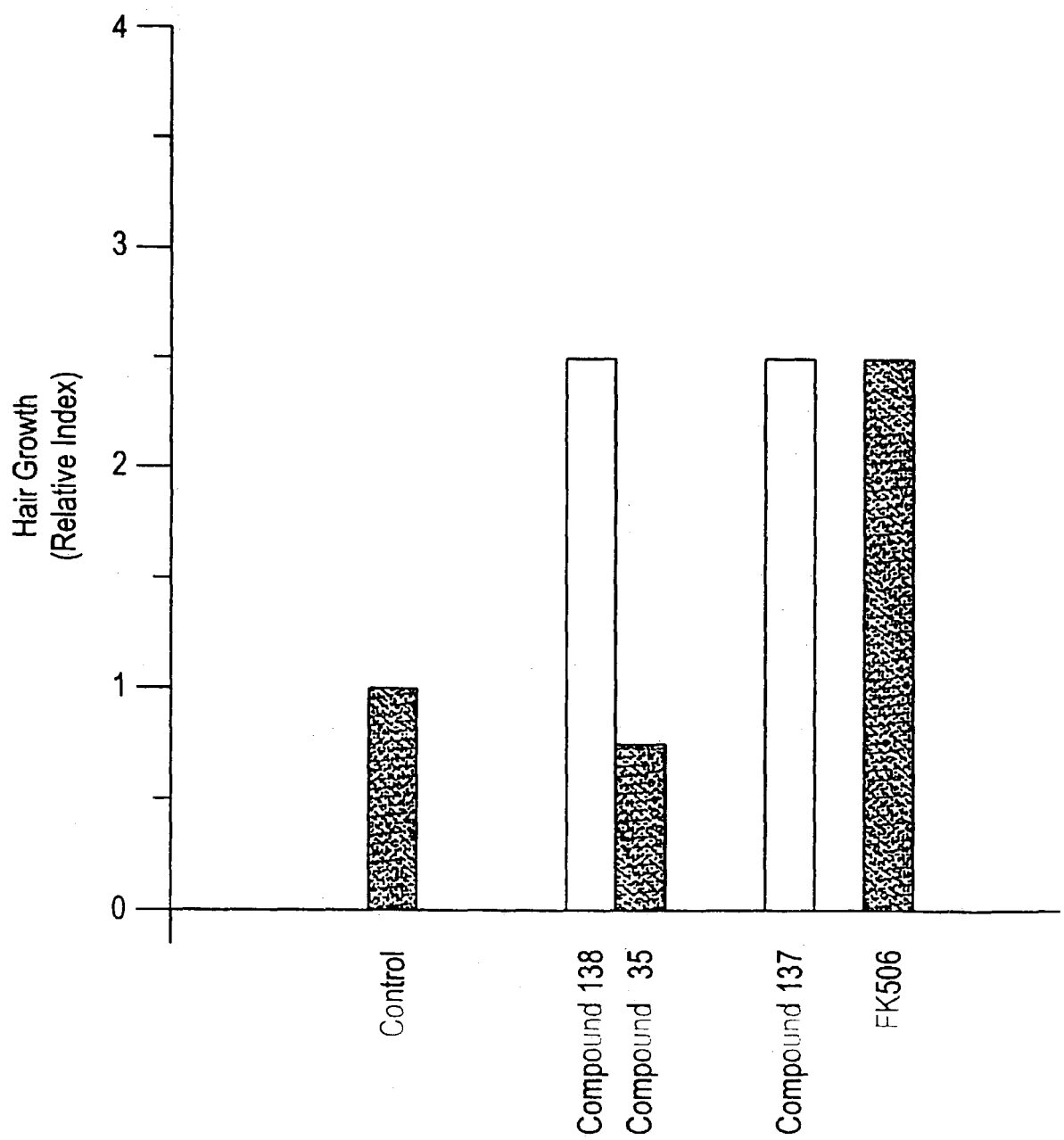
FIG. 3 is a bar graph illustrating relative hair growth on shaved mice treated with N-heterocyclic carboxylic acids or carboxylic acid isosteres at 1 μmole per milliliter three times per week. Hair growth was evaluated after 14 days of treatment.

In contrast, FIG. 3 shows that animals treated for 2 weeks with the N-heterocyclic carboxylic acid compounds i.e. compound F, compound G, and compound K exhibited dramatic hair growth, covering greater than 25% of the shaved area in all animals for two of the compounds.

FIG. 3 shows the relative hair growth on shaven C57 black 6 mice 14 days after being treated with N-heterocyclic carboxylic acids or carboxylic acid isosteres. The mice had a 2×2 inch region on their backside shaved to remove all hair. Care was taken not to nick or cause abrasion to the underlying dermal layers. Compounds at a concentration of 1 μmole per milliliter were carefully applied to the shaved area of the mice (5 mice per group) three times per week. Hair growth was evaluated 14 days after initiation of drug treatment. The relative scale for assessing hair growth is as follows:

| 0 = | no growth; |
| --- | --- |
| 1 = | beginning of growth in small tufts; |
| 2 = | hair growth covering over <25% of shaved area; |
| 3 = | hair growth covering over >25% of shaved area, but less than 50% of shaved area; |
| 4 = | hair growth covering over >50% of shaved area, but less than 75% of shaved area; |
| 5 = | complete hair growth of shaved area. |

The following examples are illustrative of preferred embodiments of the invention and are not to be construed as limiting the invention thereto. All polymer molecular weights are mean average molecular weights. All percentages are based on the percent by weight of the final delivery system or formulation prepared unless otherwise indicated and all totals equal 100% by weight.

EXAMPLES

The inventive compounds may be prepared by a variety of synthetic sequences that utilize established chemical transformations. An exemplary general pathway to the present compounds is described in Scheme I, Scheme II, and Scheme III.

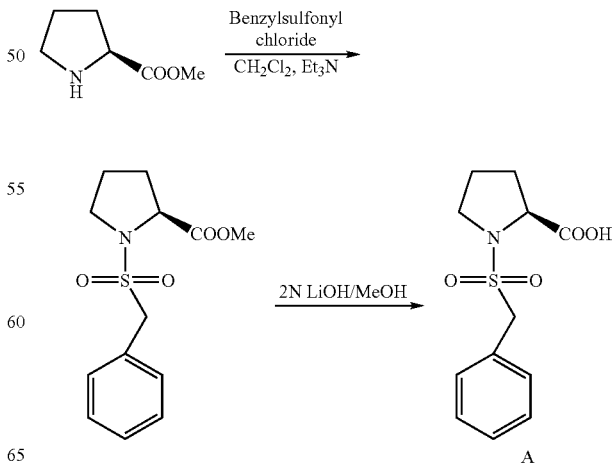

SCHEME I

SCHEME II

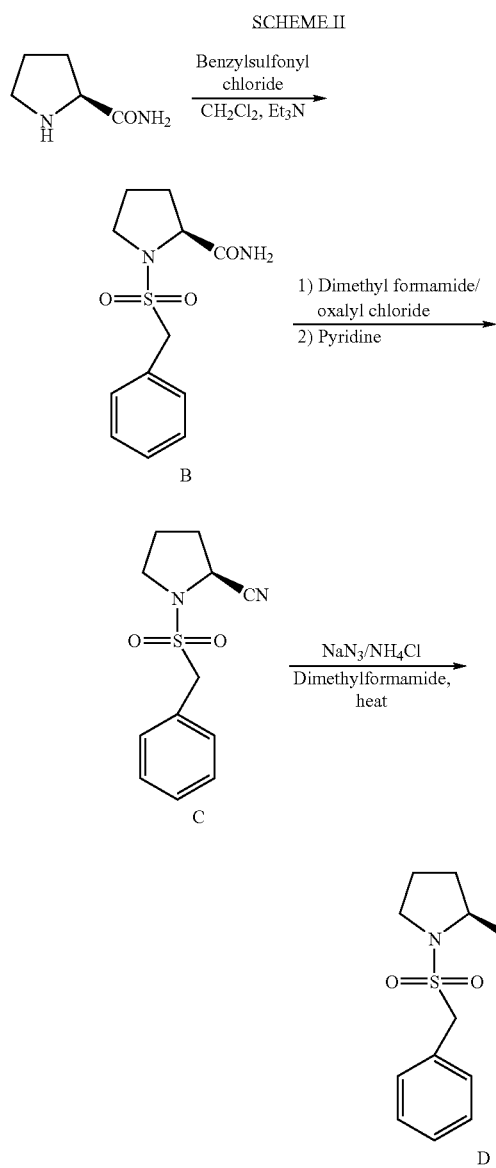

SCHEME III

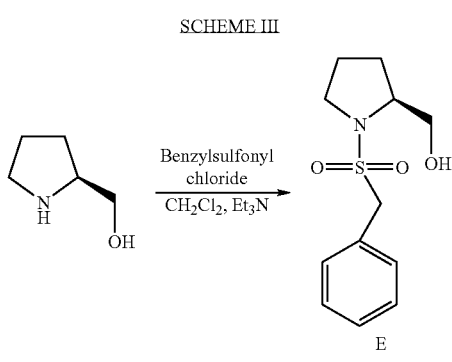

Example 1

Synthesis of (2S)-N-(benzylsulfonyl)-2-pyrrolidinecarboxylic Acid (Table I Compound 1) (Table II and Scheme I Compound A)

To a cooled (0° C.) solution of proline methyl ester hydrochloride salt (5.0 g; 30.19 mmol) in 200 mL of methylene chloride was added triethylamine (35 mL) and benzenesulfonyl chloride (5.75 g; 30.19 mmol). The mixture was stirred for one hour at 0° C. and then washed with 2×100 mL of water. The organic phase was dried and concentrated. Chromatography eluting with 50% EtOAc/hexane delivered 8.14 g (5%) of the N-sulfonamide methyl ester, which was dissolved in 120 mL of methanol, cooled to 0° C., and treated with 40 mL of 1 N lithium hydroxide. The mixture was stirred for 1 hour at 0° C. and then overnight at room temperature. After making the reaction mixture acidic (pH 1) with 1 N HCl, the product was extracted into metylene chloride and dried and concentrated to yield 4.25 g of (2S)-N-(benzylsulfonyl)-2-pyrrolidinecarboxylic acid (A) as a white solid, $^1$H NMR (CDCl$_3$, 400 MHz): d 1.85–1.90 (m, 2H); 2.08 (m, 1H); 2.18 (m, 1H); 3.04 (m, 1H); 3.27 (m, 1H); 4.32–4.35 (m, 2H); 4.45 (m, 1H); 4.45 (m, 2H); 7.36 (m, 3H); 7.48 (m, 2H); 10.98 (br, 1H).

Example 2

Synthesis of (2S)-1-(phenylmethylsulfonyl)-2-hydroxymethyl pyrrolidine (Compound 95) (Scheme III Compound E)

To a solution of (S)-(+)-2-pyrrolidinemethyanol (1.01 g, 10 mmol) and triethylamine (1.5 ml, 11 mmol) in 30 ml methylene chloride was added 1.9 g (10 mmol) α-toluenesulfonyl chloride at 0° C. with stirring. The reaction was gradually warmed up to room temperature and stirred overnight. The mixture was diluted with water, and extracted into 200 ml methylene chloride. The organic extract was concentrated and further purified by silica gel to give 1.5 g product as a white solid (58.9% yield). $^1$H NMR (CDCl$_3$): d 01.71–1.88 (m, 4H); 2.05 (br, 1H, OH); 3.22 (m, 2H); 3.47 (m, 2H); 3.67 (m, 1H); 4.35 (s, 2H); 7.26–7.44 (m, 5H, aromatic).

Example 3

Synthesis of (2S)-1-(phenylmethyl)sulfonyl-2-pyrrolidinecarboxamide (Compound 96) (Scheme II Compound B)

To a solution of L-prolinamde (2.28 g, 20 mmol) and triethylamine (5.76 ml, 42 mmol) in 40 ml methylene chloride was added 3.92 g (20 mmol) α-toluenesulfonyl chloride at 0° C. with stirring. The reaction was gradually warmed up to room temperature and stirred overnight. The mixture was diluted with water, and extracted into 200 ml methylene chloride. The organic extract was concentrated and further purified by silica gel to give 3.0 g product as a white solid (55.7% yield). $^1$H NMR (CDCl$_3$): d 01.89 (m, 3H); 2.25 (m, 1H); 3.40 (m, 1H); 3.50 (m, 1H); 3.96 (m, 1H); 4.35 (s, 2H); 7.39–7.45 (m, 5H, aromatic).

Example 4

Synthesis of (2S)-1-(phenylmethyl)sulfonyl-2pyrrolidinecarbonitrile (Compound 97) (Scheme II Compound C)

To a solution of 0.67 ml DMF (8.7 mmol) in 10 ml acetonitrile at 0° C. was added 0.70 ml (8.0 mmol) oxalyl chloride. A white precipitate was formed immediately and was accompanied by gas evolution. When complete, a solution of 2.0 g (7.5 mmol) of (2S)-1-(phenylmethyl)sulfonyl-2-pyrrolidinecarboxamide in 5.0 ml acetonitrile was added. When the mixture became homogeneous, 1.35 ml (16.5 mmol) pyridine was added. After 5 min., the mixture was diluted with water, and extracted by 200 ml ethyl acetate. The organic layer was concentrated and further purified by silica gel to give 1.5 g product as a white solid (80% yield). $^1$H NMR (CDCl$_3$): d 01.92 (m, 2H); 2.01 (m, 1H); 2.11 (m, 1H); 3.45 (m, 2H); 4.35 (s, 2H); 4.65 (m, 1H); 7.26–7.45 (m, 5H, aromatic).

Example 5

Syntheses of (2S)-1-(phenylmethyl)sulfonyl-2-pyrrolidinetetrazole (Compound 4) (Scheme II Compound D)

A mixture of (2S)-1-(phenylmethyl)sulfonyl-2-pyrrolidinecarbonitrile (250 mg, 1 mmol), NaN$_3$ (81 mg, 1.3 mmol) and NH$_4$Cl (70 mg, 1.3 mmol) in 3 ml DMF was stirred at 130° C. for 16 hours. The mixture was concentrated and purified by silica gel to give 120 mg product as a white solid (41.1% yield). $^1$H NMR (CDCl$_3$): d 01.95 (m, 2H); 2.21 (m, 1H); 2.90 (m, 1H); 3.40 (m, 2H); 4.27 (s, 2H); 5.04 (m, 1H); 7.36–7.41 (m, 5H, aromatic); 8.05 (s, 1H, NH).

Example 6

A lotion comprising the following composition may be prepared.

|  | (%) |
|---|---|
| 95% Ethanol | 80.0 |
| an N-linked sulfonamide of N-heterocyclic carboxylic acid or carboxylic acid isostere | 10.0 |
| α-Tocopherol acetate | 0.01 |
| Ethylene oxide (40 mole) adducts of hardened castor oil | 0.5 |
| purified water | 9.0 |
| perfume and dye | q.s. |

Into 95% ethanol are added an N-linked sulfonamides of N-heterocyclic carboxylic acid or carboxylic acid isostere, α-tocopherol acetate, ethylene oxide (40 is mole) adducts of hardened castor oil, perfume and a dye. The resulting mixture is stirred and dissolved, and purified water is added to the mixture to obtain a transparent liquid lotion.

5 ml of the lotion may be applied once or twice per day to a site having marked baldness or alopecia.

Example 7

A lotion comprising the following composition shown may be prepared.

|  | (%) |
|---|---|
| 95% Ethanol | 80.0 |
| an N-linked sulfonamide of N-heterocyclic carboxylic acid or carboxylic acid isostere | 0.005 |
| Hinokitol | 0.01 |
| Ethylene oxide (40 mole) adducts of hardened castor oil | 0.5 |
| Purified water | 19.0 |
| Perfume and dye | q.s. |

Into 95% ethanol are added an N-linked sulfonamides of N-heterocyclic carboxylic acid or carboxylic acid isostere, hinokitol, ethylene oxide (40 mole) adducts of hardened castor oil, perfume, and a dye. The resulting mixture is stirred, and purified water is added to the mixture to obtain a transparent liquid lotion.

The lotion may be applied by spraying once to 4 times per day to a site having marked baldness or alopecia.

Example 8

An emulsion may be prepared from A phase and B phase, having the following compositions.

|  | (%) |
|---|---|
| (A phase) |  |
| Whale wax | 0.5 |
| Cetanol | 2.0 |
| Petrolatum | 5.0 |
| Squalane | 10.0 |
| Polyoxyethylene (10 mole) monostearate | 2.0 |
| Sorbitan monooleate | 1.0 |
| an N-linked sulfonamide of N-heterocyclic carboxylic acid or carboxylic acid isostere | 0.01 |
| (B phase) |  |
| Glycerine | 10.0 |
| Purified water | 69.0 |
| Perfume, dye, and preservative | q.s. |

The A phase and the B phase are respectively heated and melted and maintained at 80° C. Both phases are then mixed and cooled under stirring to normal temperature to obtain an emulsion.

The emulsion may be applied by spraying once to 4 times per day to a site having marked baldness or alopecia.

Example 9

A cream may be prepared from A phase and B phase having the following compositions.

|  | (%) |
|---|---|
| (A Phase) |  |
| Fluid paraffin | 5.0 |
| Cetostearyl alcohol | 5.5 |

-continued

| | (%) |
|---|---|
| Petrolatum | 5.5 |
| Glycerine monostearate | 33.0 |
| Polyoxyethylene (20 mole) 2-octyldodecyl ether | 3.0 |
| Propylparaben | 0.3 |
| (B Phase) | |
| an N-linked sulfonamide of N-heterocyclic carboxylic acid or carboxylic acid isostere | 0.8 |
| Glycerine | 7.0 |
| Dipropylene glycol | 20.0 |
| Polyethylene glycol 4000 | 5.0 |
| Sodium Hexametaphosphate | 0.005 |
| Purified water | 44.895 |

The A phase is heated and melted, and maintained at 70° C. The B phase is added into the A phase and the mixture is stirred to obtain an emulsion. The emulsion is then cooled to obtain a cream.

The cream may be applied once to 4 times per day to a site having marked baldness or alopecia.

Example 10

A liquid comprising the following composition may be prepared.

| | (%) |
|---|---|
| Polyoxyethylene butyl ether | 20.0 |
| Ethanol | 50.0 |
| an N-linked sulfonamide of N-heterocyclic carboxylic acid or carboxylic acid isostere | 0.001 |
| Propylene glycol | 5.0 |
| Polyoxyethylene hardened castor oil derivative (ethylene oxide 80 mole adducts) | 0.4 |
| Perfume | q.s. |
| Purified water | q.s. |

Into ethanol are added polyoxypropylene butyl ether, propylene glycol, polyoxyethylene hardened castor oil, an N-linked sulfonamide of N-heterocyclic carboxylic acid or carboxylic acid isostere, and perfume. The resulting mixture is stirred, and purified water is added to the mixture to obtain a liquid.

The liquid may be applied once to 4 times per day to a site having marked baldness or alopecia.

Example 11

A shampoo comprising the following composition may be prepared.

| | (%) |
|---|---|
| Sodium laurylsulfate | 5.0 |
| Triethanolamine laurylsulfate | 5.0 |
| Betaine lauryldimethylaminoacetate | 6.0 |
| Ethylene glycol distearate | 2.0 |
| Polyethylene glycol | 5.0 |
| an N-linked sulfonamide of N-heterocyclic carboxylic acid or carboxylic acid isostere | 5.0 |
| Ethanol | 2.0 |
| Perfume | 0.3 |
| Purified water | 69.7 |

Into 69.7 of purified water are added 5.0 g of sodium laurylsulfate, 5.0 g of triethanolamine laurylsulfate, 6.0 g of betaine lauryldimethyl-aminoacetate. Then a mixture obtained by adding 5.0 g of an N-linked sulfonamide of N-heterocyclic carboxylic acid or carboxylic acid isostere, 5.0 g of polyethylene glycol, and 2.0 g of ethylene glycol distearate to 2.0 g of ethanol, followed by stirring, and 0.3 g of perfume are successively added. The resulting mixture is heated and subsequently cooled to obtain a shampoo.

The shampoo may be used on the scalp once or twice per day.

Example 12

A patient is suffering from alopecia senilis. An N-linked sulfonamide of N-heterocyclic carboxylic acid or carboxylic acid isostere, or a pharmaceutical composition comprising the same, may be administered to the patient. Increased hair growth is expected to occur following treatment.

Example 13

A patient is suffering from male pattern alopecia. An N-linked sulfonamide of N-heterocyclic carboxylic acid or carboxylic acid isostere, or a pharmaceutical composition comprising the same may be administered to the patient. Increased hair growth is expected to occur following treatment.

Example 14

A patient is suffering from alopecia areata. An N-linked sulfonamide of N-heterocyclic carboxylic acid or carboxylic acid isostere, or a pharmaceutical composition comprising the same, may be administered to the patient. Increased hair growth is expected to occur following treatment.

Example 15

A patient is suffering from hair loss caused by skin lesions. An N-linked sulfonamide of N-heterocyclic carboxylic acid or carboxylic acid isostere, or a pharmaceutical composition comprising the same, may be administered to the patient. Increased hair growth is expected to occur following treatment.

Example 16

A patient is suffering from hair loss caused by tumors. An N-linked sulfonamide of N-heterocyclic carboxylic acid or carboxylic acid isostere, or a pharmaceutical composition comprising the same, may be administered to the patient. Increased hair growth is expected to occur following treatment.

Example 17

A patient is suffering from hair loss caused by a systematic disorder, such as a nutritional disorder or an internal

29 secretion disorder. An N-linked sulfonamide of N-heterocyclic carboxylic acid or carboxylic acid isostere, or a pharmaceutical composition comprising the same, may be administered to the patient. Increased hair growth is expected to occur following treatment.

Example 18

A patient is suffering from hair loss caused by chemotherapy. An N-linked sulfonamide of N-heterocyclic carboxylic acid or carboxylic acid isostere, or a pharmaceutical composition comprising the same, may be administered to the patient. Increased hair growth is expected to occur following treatment.

Example 19

A patient is suffering from hair loss caused by radiation. An N-linked sulfonamide of N-heterocyclic carboxylic acid or carboxylic acid isostere, or a pharmaceutical composition comprising the same may, be administered to the patient. Increased hair growth is expected to occur following treatment.

Example 20

A patient is suffering from a neurodegenerative disease. A carboxylic acid or carboxylic acid isostere of an N-heterocyclic ring or a pharmaceutical composition comprising the same is administered. It would be expected that the patient would improve their condition or recover.

Example 21

A patient is suffering from a neurological disorder. A carboxylic acid or carboxylic acid isostere of an N-heterocyclic ring or pharmaceutical compositions comprising same is administered. It would be expected that the patient would improve their condition or recover.

Example 22

A patient is suffering from stroke. A carboxylic acid or carboxylic acid isostere of an N-heterocyclic ring or pharmaceutical compositions comprising same is administered. It would be expected that the patient would improve their condition or recover.

Example 23

A patient is suffering from Parkinson's Disease. A carboxylic acid or carboxylic acid isostere of an N-heterocyclic ring or pharmaceutical compositions comprising same is administered. It would be expected that the patient would improve their condition or recover.

Example 24

A patient is suffering from Alzheimer's Disease. A carboxylic acid or carboxylic acid isostere of an N-heterocyclic ring or pharmaceutical compositions comprising same is administered. It would be expected that the patient would improve their condition or recover.

30

Example 25

A patient is suffering from a peripheral neuropathy. A carboxylic acid or carboxylic acid isostere of an N-heterocyclic ring or pharmaceutical compositions comprising same is administered. It would be expected that the patient would improve their condition or recover.

Example 26

A patient is suffering from amyotrophic lateral sclerosis. A carboxylic acid or carboxylic acid isostere of an N-heterocyclic ring or pharmaceutical compositions comprising same is administered. It would be expected that the patient would improve their condition or recover.

Example 27

A patient is suffering from a spinal injury. A carboxylic acid or carboxylic acid isostere of an N-heterocyclic ring or pharmaceutical compositions comprising same is administered. It would be expected that the patient would improve their condition or recover.

Example 28

A patient is at risk of suffering from a neurodegenerative disease or neurological disorder. A carboxylic acid or carboxylic acid isostere of an N-heterocyclic ring or a pharmaceutical composition comprising the same is prophelactically administered.

It would be expected that the patient would be prevented from some or all of the effects of the disease or disorder, or would significally improve their condition or recover over patients who were not pre-treated.

The invention being thus described, it will be obvious that the same may be varied in many ways. Such variations are not to be regarded as a departure from the spirit and scope of the invention and all such modification are intended to be included within the scope of the following claims.

What is claimed is:

1. A compound of formula (I):

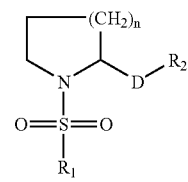

where
n is 1;
$R_1$ is selected from the group consisting of hydrogen, $C_1$–$C_9$ straight or branched chain alkyl, $C_3$–$C_9$ straight or branched chain alkenyl, aryl, heteroaryl, carbocycle, and heterocycle;
D is selected from the group consisting of a bond, $C_1$–$C_{10}$ straight or branched chain alkylene, $C_2$–$C_{10}$ alkenylene, and $C_2$–$C_{10}$ alkynylene;
$R_2$ is selected from the group consisting of:

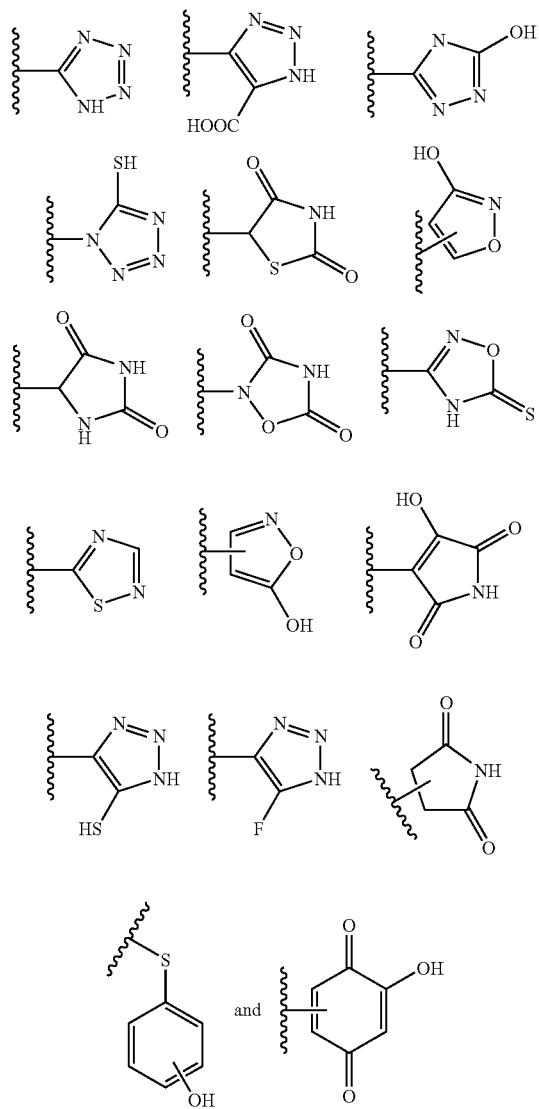

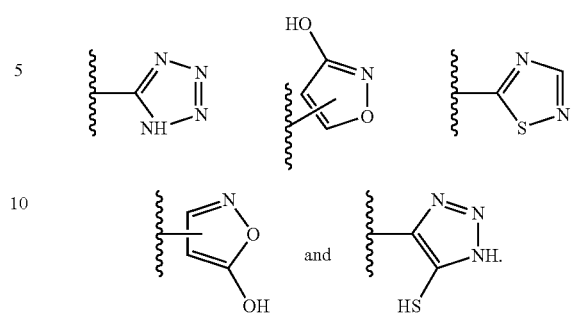

4. A compound selected from the group consisting of (2S)-1-(phenylmethyl)sulfonyl-2-hydroxymethyl pyrrolidine, (2S)-1-(phenylmethyl)sulfonyl-2-pyrrolidinetetrazole, and the compounds of formula (I):

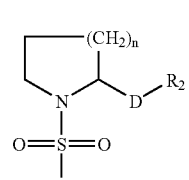

wherein n, D, $R_2$ and $R_1$ are:

| n | D | $R_2$ | $R_1$ |
|---|------|----------|--------|
| 1 | bond | Tetrazole | Benzyl, |
| 1 | bond | | Benzyl, |
| 1 | bond | | Benzyl, |
| 1 | bond | | Benzyl, |
| 1 | bond | | Benzyl, |
| 1 | bond | | Benzyl, | wherein for $R_1$ said alkyl, alkenyl, alkylene, alkenylene, alkynylene, aryl, heteroaryl. carbocycle, or heterocycle is optionally substituted with one or more substituents selected from $R_3$, where $R_3$ is selected from the group consisting of hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, heteroaryl, carbocycle, heterocycle, and $CO_2R_4$ where $R_4$ is selected from the group consisting hydrogen, $C_1$–$C_9$ straight or branched chain alkyl, and $C_2$–$C_9$ straight or branched chain alkenyl;

or a pharmaceutically acceptable salt or solvate thereof.

2. The compound of claim 1, wherein the compound is non-immunosuppressive.

3. A compound according to claim 1, wherein $R_2$ is selected from the group consisting of

-continued

| n | D | R₂ | R₁ |
|---|---|---|---|
| 1 | bond | (thiazolidine-2,4-dione) | Benzyl, |
| 1 | bond | (3-hydroxyisoxazole) | Benzyl, |
| 1 | bond | (hydantoin) | Benzyl, |
| 1 | bond | (5-hydroxyisoxazole) | Benzyl, |
| 1 | bond | (3-hydroxy-pyrrole-2,5-dione) | Benzyl, |
| 1 | bond | (5-mercapto-triazole) | Benzyl, |
| 1 | bond | (5-fluoro-triazole) | Benzyl, |
| 1 | bond | (1,3,4-oxadiazolidine-2,5-dione) | Benzyl, |
| 1 | bond | (3-ethyl-1,2,4-oxadiazole) | Benzyl, |
| 1 | bond | (5-thioxo-1,2,4-oxadiazolidine) | Benzyl, |

-continued

| n | D | R₂ | R₁ |
|---|---|---|---|
| 1 | bond | (3-methyl-1,2,4-thiadiazole) | Benzyl, |
| 1 | bond | (pyrrolidine-2,5-dione) | Benzyl, |
| 1 | bond | (2-hydroxyphenylthio) | Benzyl, and |
| 1 | bond | (2-hydroxy-cyclohexa-2,5-diene-1,4-dione) | Benzyl. |

5. A pharmaceutical composition, comprising:

a) an effective amount of a compound having formula (I):

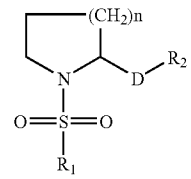

where n is 1;

R₁ is selected from the group consisting of hydrogen, $C_1$–$C_9$ straight or branched chain alkyl, $C_2$–$C_9$ straight or branched chain alkenyl, aryl, heteroaryl, carbocycle, and heterocycle;

D is selected from the group consisting of a bond, $C_1$–$C_{10}$ straight or branched chain alkylene, $C_2$–$C_{10}$ alkenylene, and $C_2$–$C_{10}$ alkynylene;

R₂ is selected from the group consisting of:

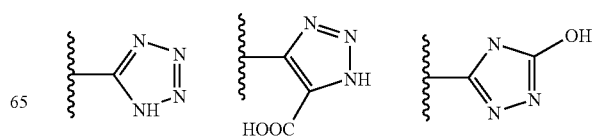

-continued

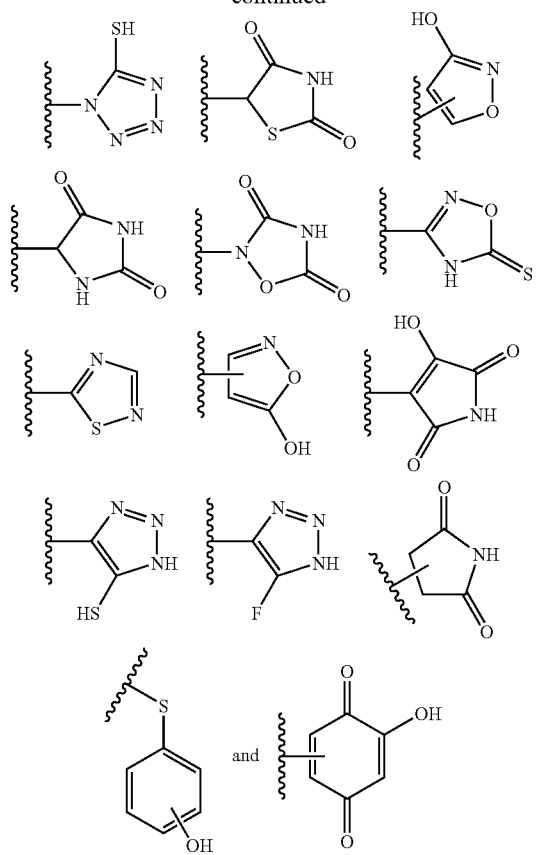

wherein for $R_1$ said alkyl, alkenyl, alkylene, alkenylene, alkynylene, aryl, heteroaryl, carbocycle, or heterocycle is optionally substituted with one or more substituents selected from $R_3$, where $R_3$ is selected from the group consisting of hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, sulfhydryl, thioalkyl, alkylthio, sulfonyl, $C_1$–$C_6$ straight or branched chain alkyl, $C_2$–$C_6$ straight or branched chain alkenyl or alkynyl, aryl, heteroaryl, carbocycle, heterocycle, and $CO_2R_4$ where $R_4$ is selected from the group consisting of hydrogen, $C_1$–$C_9$ straight or branched chain alkyl, and $C_2$–$C_9$ straight or branched chain alkenyl;

or a pharmaceutically acceptable salt or solvate thereof; and b) a pharmaceutically acceptable carrier.

6. The pharmaceutical composition of claim 5, wherein the compound is selected from the group consisting of compounds of formula (I):

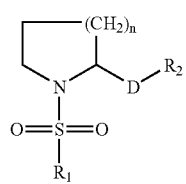

wherein n, D, $R_2$ and $R_1$ are:

| n | D | $R_2$ | $R_1$ |
|---|---|---|---|
| 1 | bond | Tetrazole | Benzyl, |
| 1 | bond | ![tetrazole-HN] | Benzyl, |
| 1 | bond | ![triazole-diMe] | Benzyl, |
| 1 | bond | ![triazole-HOOC] | Benzyl, |
| 1 | bond | ![triazol-OH] | Benzyl, |
| 1 | bond | ![tetrazole-SH] | Benzyl, |
| 1 | bond | ![thiazolidinedione] | Benzyl, |
| 1 | bond | ![isoxazol-OH] | Benzyl, |
| 1 | bond | ![hydantoin] | Benzyl, |
| 1 | bond | ![isoxazolone] | Benzyl, |
| 1 | bond | ![pyrroledione-OH] | Benzyl, |

-continued
| n | D | R₂ | R₁ |
|---|---|---|---|
| 1 | bond | 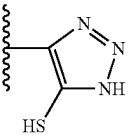 | Benzyl, |
| 1 | bond | 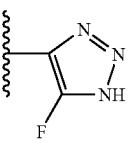 | Benzyl, |
| 1 | bond | 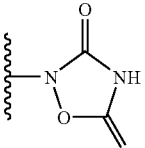 | Benzyl, |
| 1 | bond | 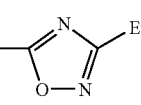 | Benzyl, |
| 1 | bond | 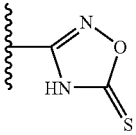 | Benzyl, |
| 1 | bond | 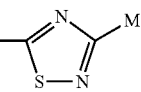 | Benzyl, |
| 1 | bond | 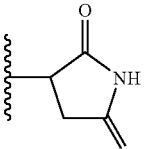 | Benzyl, |
-continued
| n | D | R₂ | R₁ |
|---|---|---|---|
| 1 | bond | 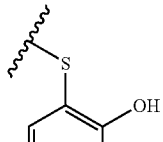 | Benzyl, and |
| 1 | bond | 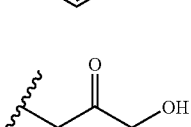 | Benzyl. |
7. A composition according to claim 5, wherein $R_2$ is selected from the group consisting of
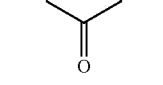 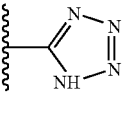 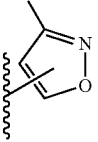
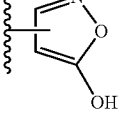 and 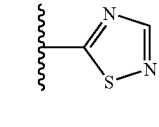
* * * * *